United States Patent
Kelly et al.

(10) Patent No.: US 8,550,314 B2
(45) Date of Patent: Oct. 8, 2013

(54) GLOVES

(75) Inventors: Patrick Kelly, Alicante (ES); Simon Mitchell Webb, Warwickshire (GB); Andrew Renfrew, Leicester (GB); Bruce Renfrew, Leicester (GB); Minghao Zhou, Leicester (GB); Shaun Phillips, Leicester (GB)

(73) Assignee: Sybre Limited (GB)

( * ) Notice: Subject to any disclaimer, the term of this patent is extended or adjusted under 35 U.S.C. 154(b) by 89 days.

(21) Appl. No.: 13/060,055

(22) PCT Filed: Aug. 20, 2009

(86) PCT No.: PCT/GB2009/002031
§ 371 (c)(1),
(2), (4) Date: May 3, 2011

(87) PCT Pub. No.: WO2010/020780
PCT Pub. Date: Feb. 25, 2010

(65) Prior Publication Data
US 2011/0204105 A1 Aug. 25, 2011

(30) Foreign Application Priority Data
Aug. 20, 2008 (GB) .................................. 0815233.2
Mar. 31, 2009 (GB) .................................. 0905593.0

(51) Int. Cl.
*A47G 25/90* (2006.01)
*A47G 25/00* (2006.01)

(52) U.S. Cl.
USPC ........................................................ 223/111

(58) Field of Classification Search
USPC .................... 223/111–119; 2/159, 169, 162, 2/16, 17
See application file for complete search history.

(56) References Cited

U.S. PATENT DOCUMENTS

| 28,927 | A | * | 6/1860 | Wheeler | 223/113 |
|---|---|---|---|---|---|
| 4,898,309 | A | * | 2/1990 | Fischer | 223/111 |
| 6,279,792 | B1 | | 8/2001 | Neal | |
| 6,419,131 | B1 | | 7/2002 | Rix | |
| 6,427,883 | B1 | * | 8/2002 | Esten | 223/111 |
| 7,070,074 | B2 | * | 7/2006 | Landsberger et al. | 223/113 |
| 7,634,862 | B2 | * | 12/2009 | Cockman | 36/138 |
| 2008/0110944 | A1 | | 5/2008 | Webb | |
| 2010/0186589 | A1 | * | 7/2010 | Johnson | 95/149 |

FOREIGN PATENT DOCUMENTS
WO    2005013842 A    2/2005

OTHER PUBLICATIONS

Held, Guenter, International Search Report for PCT/GB2009/002031, Dec. 23, 2009.

* cited by examiner

*Primary Examiner* — Ismael Izaguirre

(57) ABSTRACT

A flexible member (114) for supporting a glove in a manner whereby it can be readily donned by a user without touching the exterior of the glove. The flexible member (114) having a substantially planar glove support portion (122) which, when viewed in plan, conforms to the shape of at least part of the interior of a glove and is fittable, in use, to the interior of a glove through the cuff aperture thereof, and an attachment portion (112) by which the flexible member (114) can be held to facilitate donning of a glove and the subsequent removal of the glove support portion (122) from the cuff aperture of a glove while the glove is worn by a user. The glove support portion (122) is of sufficient flexibility to deflect around the hand of a user as said hand is inserted into a glove supported by the glove support portion (122), and further to deflect around the wrist of a user as the glove support portion (122) is removed from the glove through the cuff aperture thereof.

20 Claims, 20 Drawing Sheets

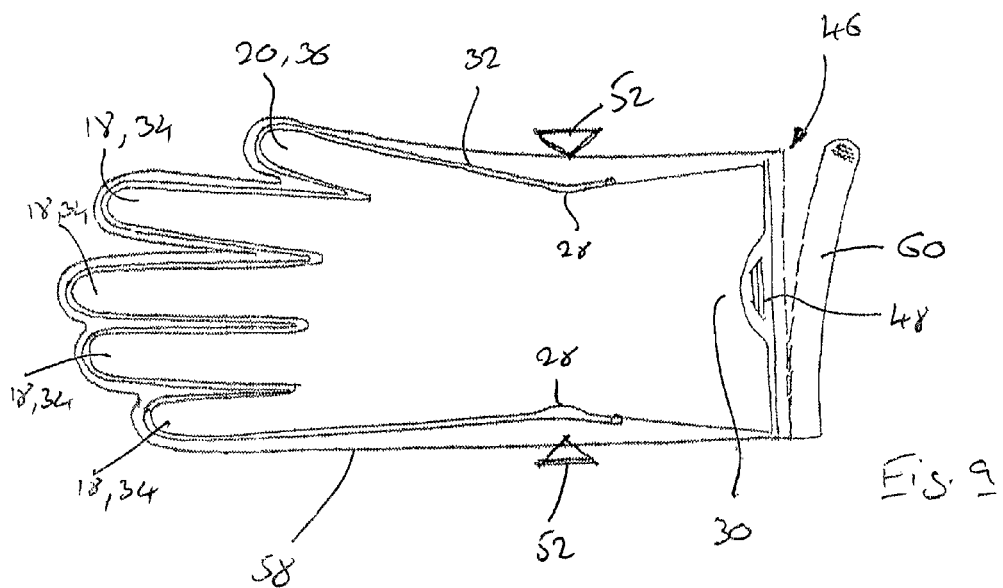
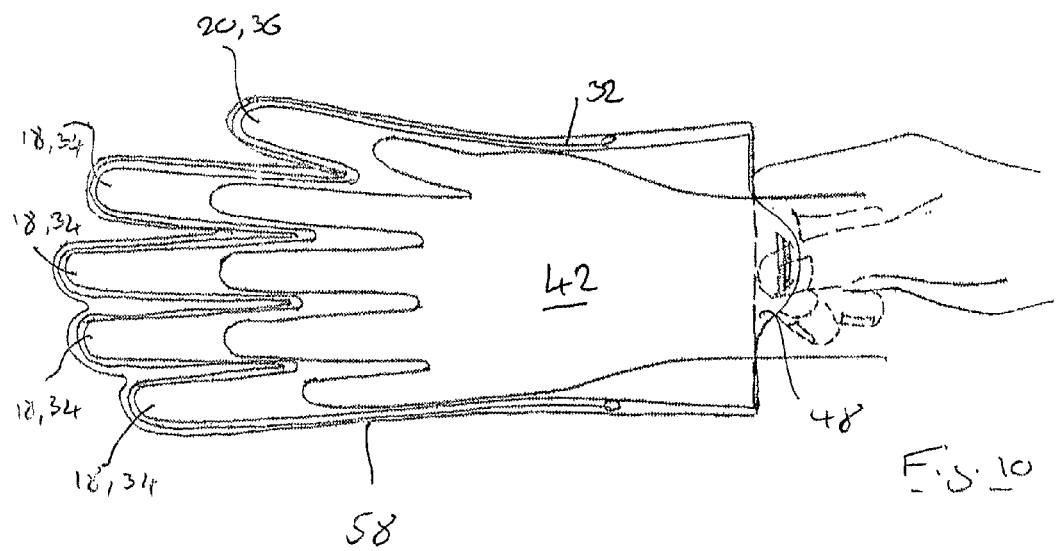

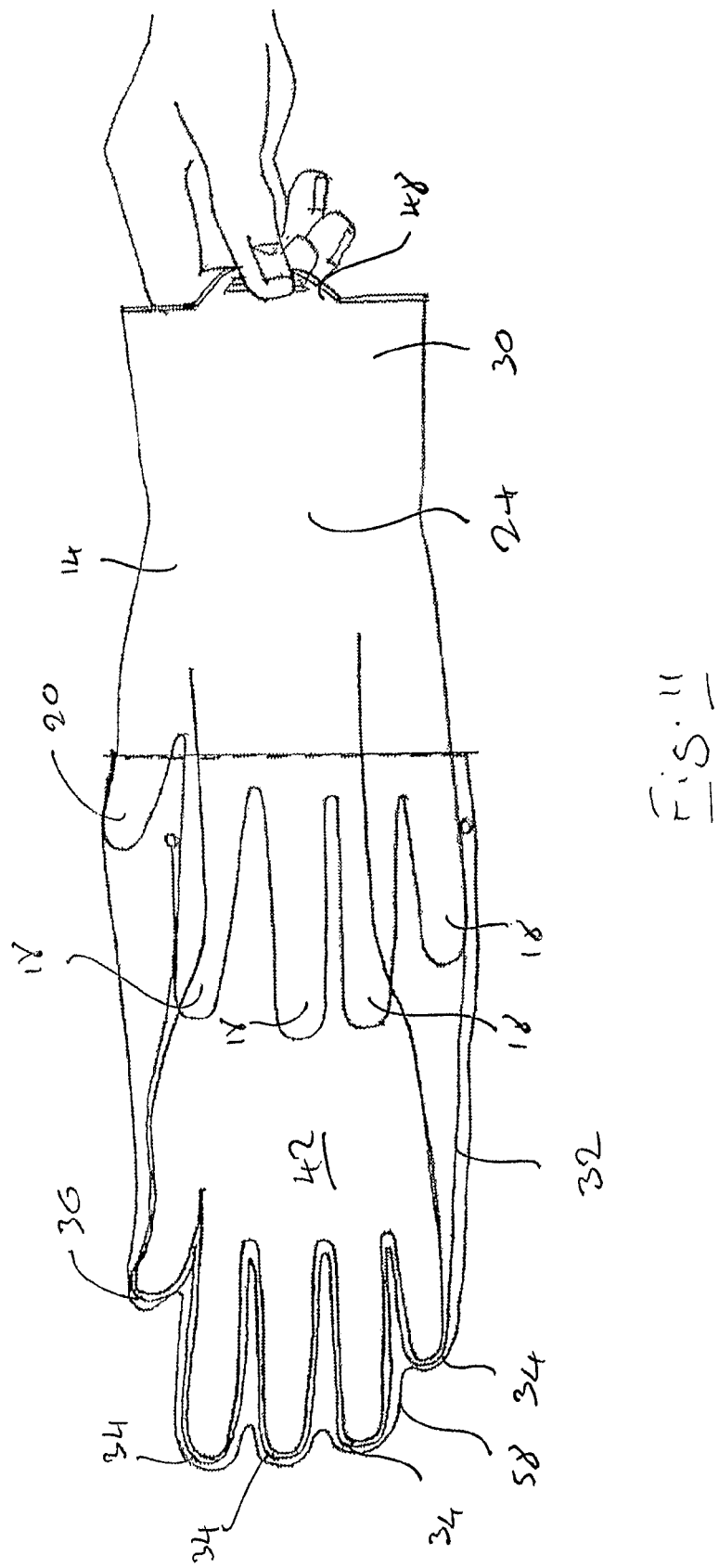

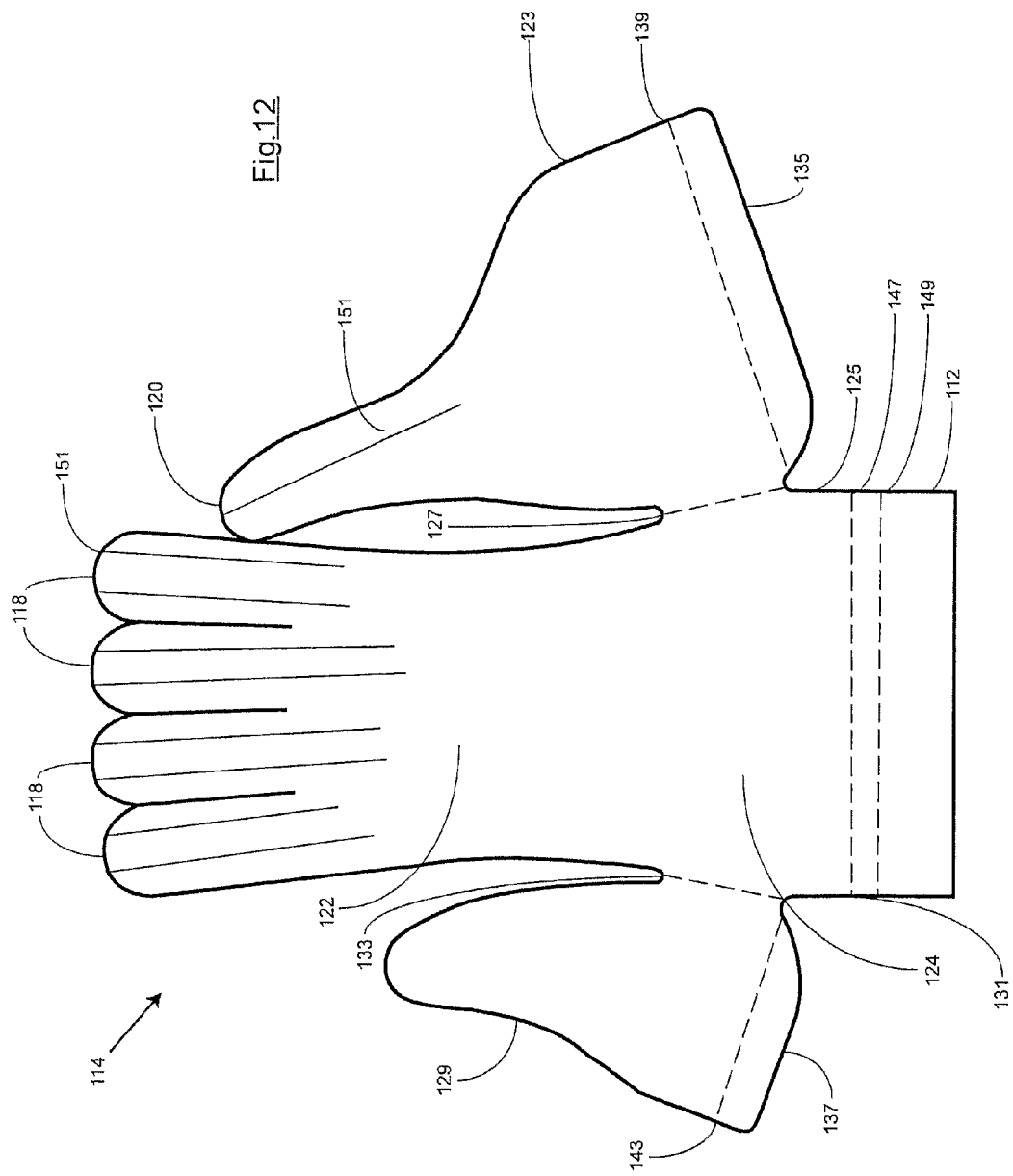

GLOVES

This is a national stage application filed under 35 USC 371 based on International Application No. PCT/GB2009/002031 filed Aug. 20, 2009 and claims priority under 35 USC 119 United Kingdom Patent Application No. GB 0815233.2, filed Aug. 20, 2008 and United Kingdom Patent Application No. GB 0905593.0, filed Mar. 31, 2009.

The present invention relates to a flexible member for holding a glove, an apparatus for donning a glove comprising the combination of a flexible member and a glove, and a method of donning a glove using the apparatus. The invention is particularly concerned, though not exclusively, with the use of the apparatus with a sterile glove to allow the glove to be put on easily whilst maintaining the sterility of the glove. The invention is equally applicable to the donning of non-sterile gloves.

Gloves, including surgical gloves, are worn in a variety of environments that demand sterility, for example, in medical, laboratory, food-preparation and manufacturing "clean room" environments. There are numerous situations in which it is important to maintain the sterility of a glove as it is being donned.

In the medical environment, gloves are worn to prevent the hands of medical professionals from contacting a patient's body during a physical examination or a surgical operation. Protective gloves, in general, are universally recognised as a major safeguard against the risk of inadvertent or accidental infection or cross contamination of patients, of the wearer of the gloves and of the medical environment.

For example, the use of a single sterile glove on the non-dominant hand may be used to feel over a vein during the performance of a venipuncture to prevent contamination of a patient's bloodstream.

In the manufacturing "clean room" environment, gloves are worn to prevent the hands of a technician from directly contacting items, such as wafers and other devices supporting highly sensitive electronic circuits. Wearing non-sterile gloves in such an environment may lead to contamination of such items, making them unsuitable for use.

It is of the utmost importance that gloves that are manufactured to be sterile are kept in a sterile condition during storage. Where gloves are initially sterile it is often highly desirable, and in some cases mandatory, that the sterility of the gloves be maintained during the donning process. Sterility of the glove can be adversely affected during the process in which the wearer puts on or dons the gloves. Accordingly, the putting on or donning process is a major point of contamination of the sterile gloves. During the donning process, the hands or other sources of contamination can contact and contaminate the sterile gloves by the inadvertent transfer of microbes or other contaminants to the sterile glove surfaces.

In the medical profession, the risk of undesirable contamination arising during the donning process is reduced by putting the glove on by using one of two generally accepted techniques for unassisted donning. These two techniques are open glove donning and closed glove donning.

The open glove donning technique now used for donning gloves, for example surgical gloves, requires that the sealed package containing the sterile gloves be carefully opened so that the inner surfaces of the package, and more particularly, the outside surfaces of the gloves contained therein, do not come in contact with any non-sterile surface. The gloves are usually packaged with their cuffs averted; that is, turned inside out and folded downwardly. To don the right glove, the wearer grasps the right glove on the fold of the averted cuff with the left hand and the right hand is inserted into the glove opening. Next, the left glove is picked up and held with the right hand by slipping the gloved fingers of that hand underneath the averted cuff while the left hand is inserted into the glove opening. To complete glove donning, the averted cuffs are carefully pulled over the distal ends of the garment's sleeves so that the entirety of the previously exposed surfaces of the averted cuffs are on the insides of the gloves and the outsides remain untouched by un-gloved hands.

In the closed glove donning technique, the gloves are handled through the fabric of the sleeve itself, for example a surgical gown sleeve. As such, the wearer's hand does not extend outside from the sleeve until the open end of the glove is actually pulled over the sleeve. The closed glove donning technique may best be conveyed by describing its current use in a surgical arena. This method assumes that the wearer is already wearing a sterile surgical gown. Accordingly, the wearer uses the left hand while keeping it within the sleeve of the gown to pick up the right glove by its averted cuff. In this manner, the glove itself is not directly touched since the left hand is shielded by the sleeve. With the right hand extended palm upward but retained within the sleeve, the left hand places the palm of the glove with fingers pointing towards the wearer against the retained palm of the right hand. The closest edge of the averted cuff is grasped by the right hand through the sleeve fabric. Next, the left hand pulls the un-grasped averted cuff edge over the right sleeve and hand. The left hand is gloved in the same manner using the gloved right hand to appropriately place the left glove and pull it over the left sleeve and hand.

Both glove donning methods entail difficulties. The open glove donning technique requires a high level of finger and hand dexterity. The closed glove donning technique suffers from finger and hand dexterity being hampered while one's fingers remain shielded by the sleeve. As would be expected by such complex procedures, they are susceptible to numerous accidental contamination possibilities, especially during times of distress and urgency. Thus, a better method is needed that enables the wearer to don gloves without using the open or closed methods but using a method which is quicker, easier, more controlled, simple to practice, preformed, sterile and which does not necessitate the help of an assistant. In addition, this method should be economically cost effective to implement and practice.

In dental care settings, where the dentist or dental assistant is obliged to work inside the mouth, post-treatment infections occur because of poor hygiene practice. For example, dental office surveys by means of hidden video cameras revealed that sampled dentists wash their hands before donning gloves in only 23% of patient contacts and changed gloves between patients in only 56% of contacts (Porter et al. British Medical Journal 1996; 312: 705). By providing an improved method of donning sterile gloves which is quicker, easier and more efficient than existing methods, dentists and dental assistants are more likely to change gloves between patient contacts and the likelihood of the gloves becoming contaminated during the donning process is reduced. This would have the effect of reducing post-treatment infections.

The magnitude of the un-sterile glove problem comes into focus when one considers:

1. Apart from designated surgical operating rooms, un-sterile examination gloves are currently estimated at being used at the rate of more than 10 billion/yr. in U.S. health care facilities.
2. Studies by trained observers in sampled intensive care units and emergency rooms reveal that health care workers wash their hands before and after each patient contact only 20-40% of the time (Wurtz et al. Am. J. Infect. Control 1994; 22: 228-230; Nystrom. Infect. Control Hosp. Epidemiol. 1994; 15: 435-436; Meengs et al. J. Emerg. Nurs. 1994; 20: 183-188).

3. A survey found that health care workers washed their hands before putting on examinations gloves, only 27 times out of a hundred (Thompson B. L. et al. Infect. Control Hosp. Epidemiol. 1997; 18: 97-103).
4. The increased use of latex gloves by health care workers to protect themselves from HIV and HBV infections has led to a false sense of security among health care workers and patients and has lead to wide-spread failure to wash hands properly and adequately during patient care (Heptonstall & Mortimer. Lancet 1995; 345: 599-600).

The above examples demonstrate that there is high prevalence of failure to wash hands properly, if at all, between patient contacts amongst health care workers and dentists. Therefore, in these situations, the risk of contamination of a sterile glove coming into contact with an unwashed hand is far higher than if the hand had been thoroughly washed. An improved method of donning a sterile glove which minimises the risk of an unwashed hand coming into contact with the sterile outer surface of the glove would significantly reduce the chances of contamination. This, in turn, would reduce the chances of post operative infection, cross contamination, etc.

In the manufacturing "clean room" environment, an improved method of donning a sterile glove would also significantly reduce the chances of contamination. In this situation, contamination might be from grease, oil or other residues on the wearers hands which could severely affect any electronic circuits or other highly sensitive electronic equipment if such contaminants were to come into contact with the electronic circuits or equipment.

As can be seen, it is highly desirable to develop an apparatus and/or method which allows the donning of sterile gloves to be quicker, easier, more controlled, simpler to practice, preformed, sterile and which does not necessitate the help of an assistant. In addition, this apparatus and/or method should be economically cost effective to implement and practice.

An object of the present invention is to minimise the risk of contamination of a sterile glove during the donning process.

A further object of the invention is to increase the speed and ease by which a glove or pair of gloves can be donned.

Another object of the invention is to reduce the temptation amongst workers in sterile environments not to use gloves or not to change their gloves by using the present invention rather than current cumbersome methods.

According to a first aspect of the present invention there is provided a flexible member for supporting a glove in a manner whereby it can be readily donned by a user without touching the exterior of the glove, the flexible member having a substantially planar glove support portion which, when viewed in plan, conforms to the shape of at least part of the interior of a glove and is fittable, in use, to the interior of a glove through the cuff aperture thereof, and an attachment portion by which the flexible member can be held to facilitate donning of a glove and the subsequent removal of the glove support portion from the cuff aperture of a glove while the glove is worn by a user, the glove support portion being of sufficient flexibility to deflect around the hand of a user as said hand is inserted into a glove supported by the glove support portion, and further to deflect around the wrist of a user as the glove support portion is removed from the glove through the cuff aperture thereof.

The glove support portion, in use, guides the hand of the user into a glove supported by the flexible member. The ability of the flexible member to deflect around the hand of a user ensures that the movement of the hand of the user into a glove is not impeded by the flexible member, nor is removal of the glove support portion from the interior of the glove after donning.

The flexible member is planar and may be manufactured from a flexible plastics material. For example, the flexible member may be formed from a sheet of plastics material by, for example, cutting. The plastics material used for the flexible member preferably has a low friction surface so as to permit the hand of a user to move relative to the flexible member without catching or snagging. The flexible member may be formed from a material other than a plastics material which exhibits similar properties. For example, the flexible member may be formed from a sheet of paper or card. In such an embodiment the card or paper may be provided with a waxed coating or may be provided with a thin external plastic layer or film. The glove support portion of the member may be provided with formations which cause the member to deflect, deform, fold or bend in a predetermined manner, in use. For example, the glove support portion may be provided with one or more score lines, indentations or slits.

The glove support portion may be provided with at least one digit portion which, in use, is received in a corresponding digit portion of a glove. The glove support portion may be provided with a thumb portion and at least one finger portion. Alternatively, the glove support portion may be provided with a thumb portion and up to four finger portions. The glove support portion of the flexible member is provided with a cuff portion to which the cuff of a glove may be mounted, in use. The cuff portion may be dimensioned such that the cuff of a glove is expanded slightly thereby when fitted to the cuff portion. It will thus be appreciated that in such an instance the inherent resilience of the glove may be employed to retain the glove to the glove support portion.

The attachment portion is preferably provided with means to locate the flexible member to a means of resisting forces applied thereto resulting from the donning of a glove. The attachment portion may be provided with a formation connectable to a fixed base. Alternatively, the attachment portion may be configured so as to be grippable by the opposite hand of a user to the hand to which a glove is to be donned.

The glove support portion is may be provided with a means to retain a cuff bead of a glove fitted to the flexible member. In such an embodiment, the glove support portion may be provided with at least one recess within which the cuff bead may be retained. In such an embodiment the glove support portion is provided with opposed recesses within which the cuff bead may be retained. For gloves which are not provided with a cuff bead, the open end of the cuff may still be retained in the at least one recess. In yet a further embodiment the glove support portion may not be provided with such recesses. In such an embodiment the glove support portion may be shaped such that a glove is retained thereto by frictional contact due to slight stretching of the glove by the glove support portion. A glove may be retained to the glove support portion by a combination of frictional contact and cuff or cuff bead retention.

According to a further aspect of the invention there is provided a device for holding a glove in a manner whereby it can be readily donned by a user without touching the exterior of the glove, the device comprising two flexible members of the type described with reference to the first aspect.

The mounting members overlie one another. The mounting members may be substantially planar and may be joined to one another at least one location. The mounting members may be joined to one another at two locations. In such an embodiment the mounting members are joined to one other at opposing locations of the glove support portion which correspond to the cuff region of a glove fitted to the device. At least one of said joins is breakable by the action of a hand of the user donning the glove According to a further aspect of the present invention there is provided an apparatus for donning a glove the apparatus comprising a flexible member or device according to the first or second aspects of the present invention and a glove mounted to the flexible member or device. In such an embodiment the apparatus may be sealed within a cover which is at least partially removable before use of the apparatus.

According to yet a further aspect of the present invention there is provided a method of donning a glove.

The flexible member is may provided with a means to hold the cuff of a glove mounted thereto in an open position. The flexible member may be provided with at least one extension of the glove support portion which, in use, corresponds to the cuff of a glove supported thereby. The at least one extension may extend laterally from an edge of the glove support portion. The at least one extension may be foldable over the glove support portion to define a mouth. The glove support portion may be provided with two extensions which extend from opposed edges thereof. Each extension may be provided with a means to releasably retain the extensions to one another. The extensions retainable to one another to define the mouth. In such an embodiment the size of the mouth may increase during a donning procedure An edge of each extension may be folded so as to define a channel, and the channel of one extension slidably retained in the channel of the other.

The glove support portion may be provided with a palm portion which, in use, is received in a corresponding palm portion of a glove. The glove support portion may be provided plurality of digit portions which, in use, are received in corresponding digit portions of a glove. The glove support portion may be provided with a thumb portion and at least one finger portion. Alternatively, the glove support portion may be provided with a thumb portion and up to four finger portions. The thumb portion may be provided the aforementioned extension which is foldable over the cuff portion.

The attachment portion is preferably provided with means to locate the flexible member to a means of resisting forces applied thereto resulting from the donning of a glove.

According to a further aspect of the present invention there is provided the combination of a flexible member of the type described above and a glove.

According to a further aspect of the present invention there is provided a container for the combination of a flexible member of the type described above and a glove, the attachment portion of the flexible member being connected to the interior of the container, the container being openable to allow access to the glove, the container being provided with attachment means to releasably attach the container to a surface.

The attachment means may comprise a region of adhesive provided on the exterior of the container. Alternatively, the attachment means may comprise a strip of hook and loop fastener material which, in use, engages with a corresponding portion of hook and loop fastener material provided on a surface. Alternatively, the container may be provided with a portion of a fastener which connects to a corresponding fastener portion at a donning location. In yet a further embodiment, there may be provided a high friction, non-slip coating on the exterior of the container which, in use, resists movement of the container over a surface upon which it rests.

The container may further be provided with a cover sheet which is attached to the container and which overlies the flexible member and glove combination. The cover sheet may be deployable to the exterior of the container.

Embodiments of the present invention will now be described with reference to the accompanying drawings in which:

FIGS. 9 to 11 show the donning of a glove;

FIG. 12 shows a plan view of a further embodiment of a glove holding member according to an aspect of the present invention;

Figure 1:
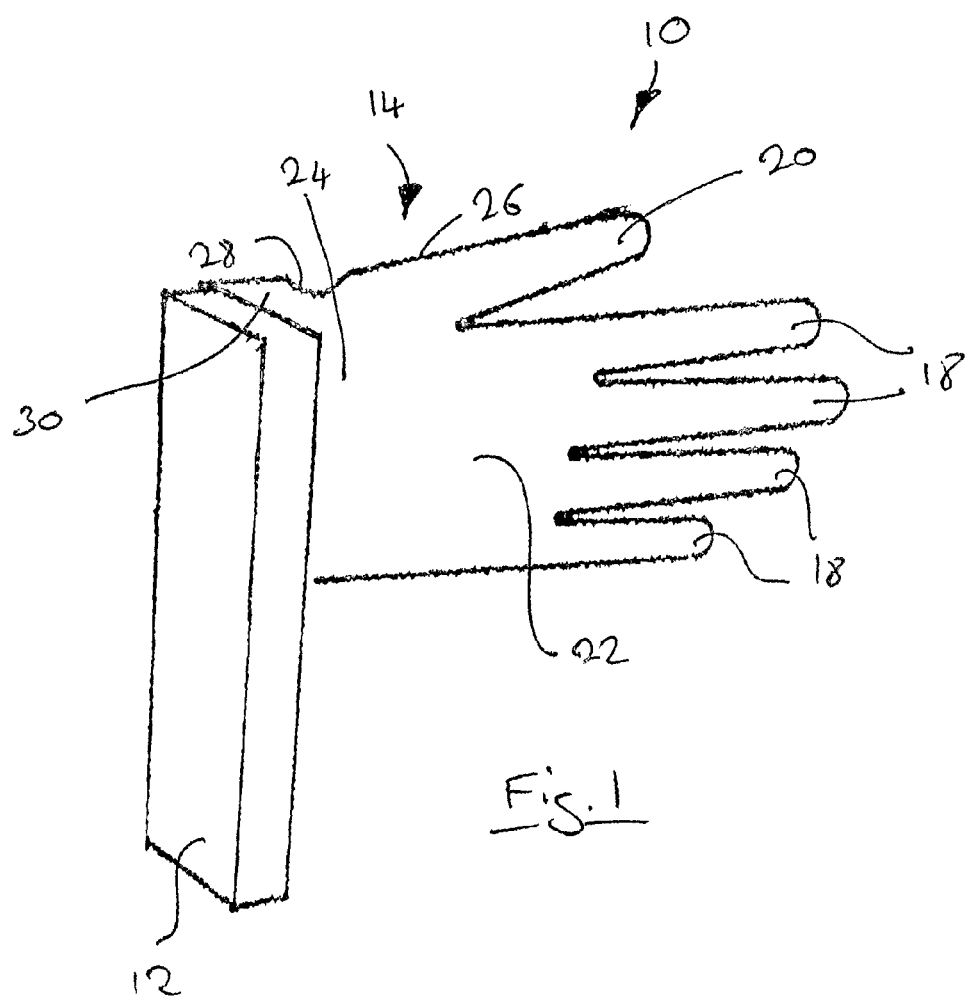
FIG. 1 shows a perspective view of a first embodiment of a glove holding device according to an aspect of the present invention.

Looking firstly at FIG. 1 there is shown part of glove holding device generally designated 10. The device 10 comprises a base 12 and a substantially hand shaped glove holding or support member 14 which extends from the base 12. In the embodiment shown the base 12 is in the form of a post to which the holding member 14 is attached. The post is used for the purpose of illustrating the need for the hand shaped holding member 14 to supported in such a manner that it can resist loads applied to it during a glove donning procedure. For example, the base 12 may form part of a glove dispenser mechanism which holds the holding member 14 and presents the glove to the user. Alternatively, the base 12 may be defined by a hand of a user gripping the holding member 14.

The holding member 14 is comprised of a substantially planar flexible sheet of material which conforms to the shape of a glove. The member 14 is provided with finger portions 18 and a thumb portion 20. The finger and thumb portions 18,20 extend from a palm portion 22, which in turn extends from a cuff portion 24 of the member 14. The edge 26 of the holding member 14 in the region of cuff portion 24 is provided with a cut out 28 which, in use, is used to locate and retain the cuff of a glove. A similar cut out (not shown) is provided on the opposing edge of the holding member 14. Extending from the cuff portion 24 of holding member 14 to the base 12 is an alignment portion 30 of the holding member 14. In use, the alignment portion 30 extends beyond the cuff of a glove and acts to guide the hand of a user into the glove.

The finger and thumb portions 18,20 are provided in a slightly splayed configuration and correspond substantially to the finger and thumb positions of a glove. The member 14 is positioned relative to the base 12 with the thumb potion 20 uppermost. In the embodiment shown the holding member 14 is sized so as to correspond to the size of the glove it is intended hold such that the glove is not stretched or tensioned when fitted to holding member 14. It will be appreciated that in an alternative embodiment the glove may be stretched slightly such that it grips the holding member 14.

The holding member 14 is formed from a flexible material such as, for example, PVC.

Figure 2:
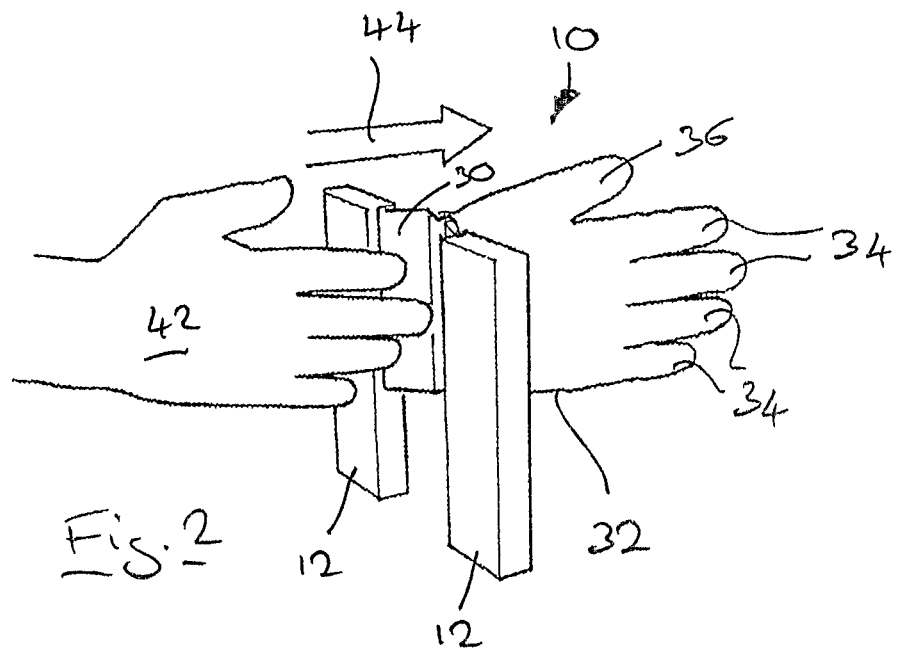
FIGS. 2 to 6 show the donning of a glove by a user.

FIGS. 2 to 6 illustrate the donning of a glove with the assistance of the device 10 shown in FIG. 1. FIG. 2 shows a glove 32 mounted between two opposing devices 10. Features of the devices described with reference to FIG. 1 are identified with like reference numerals. The glove 32 is mounted to holding members 14 such that the finger, thumb, palm and cuff portions 18,20,22,24 of the holding members 14 align with the corresponding finger, thumb, palm and cuff portions 34,36,38,40 of the glove 32. The cuff bead of the glove 32 is received in the cut-outs 28 of he members 14. The alignment portions 30 of the holding members 14 extend from the cuff aperture 41 of the glove 32 and face the user. In the embodiment shown, the alignment portions 30 are inclined relative to one another so as to present to the user a tapered channel leading to a slot defined between the cuff portions 24 of the members 14.

Figure 3:
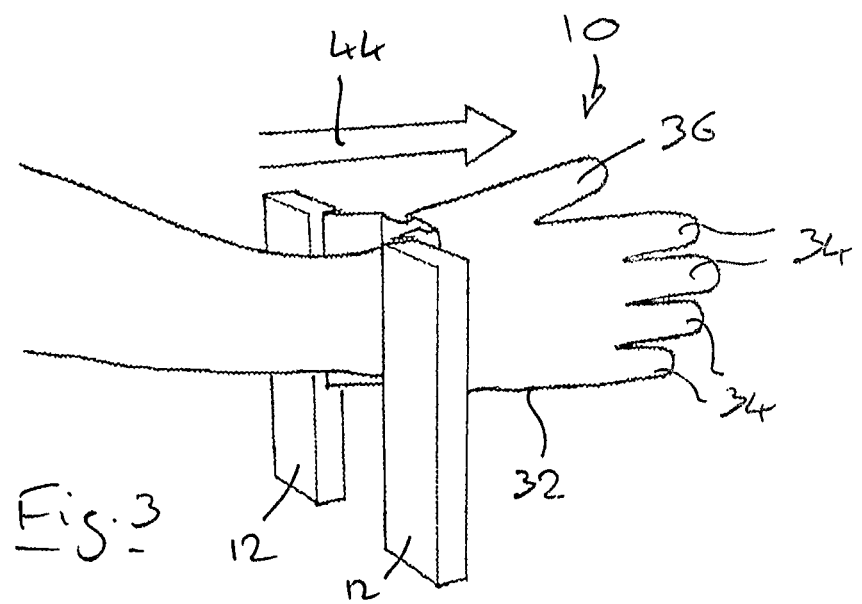
Figure 4:
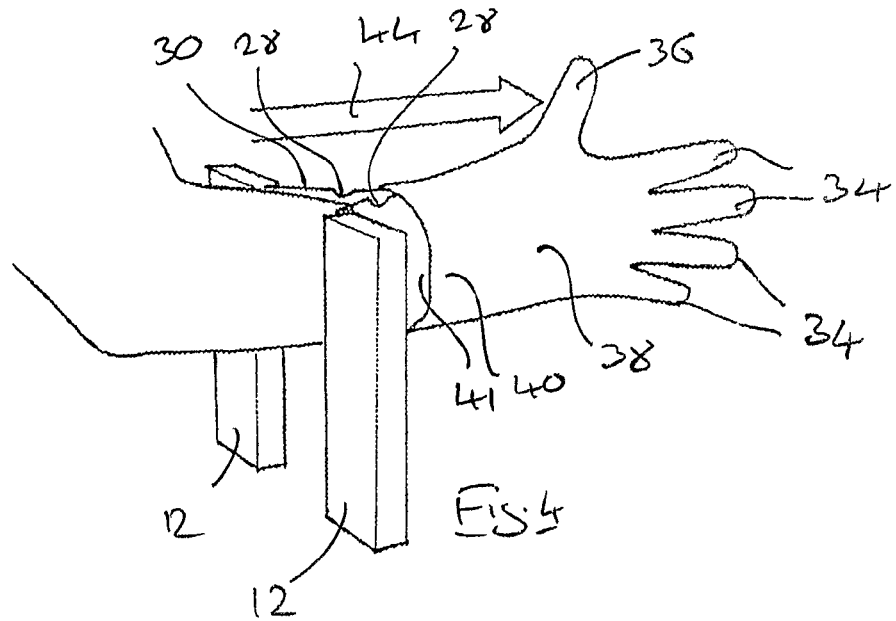

In use, a user inserts their hand 42 between the alignment portions 30 and into the slot defined between the cuff portions 24 of the members 14 as indicated by arrow 44 (FIG. 2). Continued movement of the hand 42 of the user parts the members 14 and allows the hand 42 of the user to enter the glove 32 between the members 14 (FIG. 3). The material from which the holding members 14 are formed has a low friction surface and hence does not impede the passage of the hand 42 of the user. As a result of the flexibility of the material from which the holding members 14 are made, the holding members 14 deflect around the hand 42 of the user and do not impede the movement of hand to the interior of the glove 32. The thumb and fingers of the user are guided into the corresponding portions 34,36 of the glove 32 by the thumb and finger portions 18,20 of the members 14.

Figure 5:
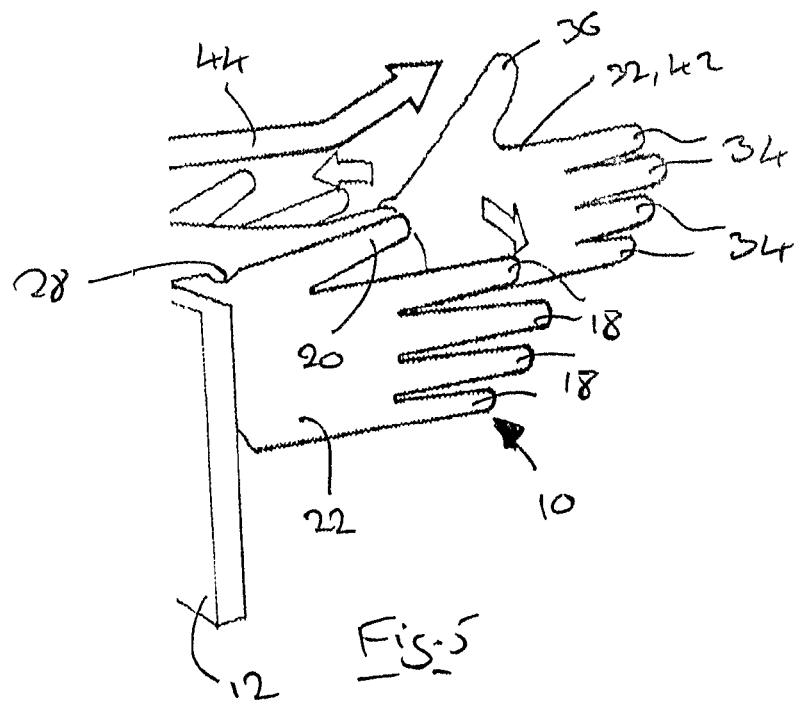
Figure 6:
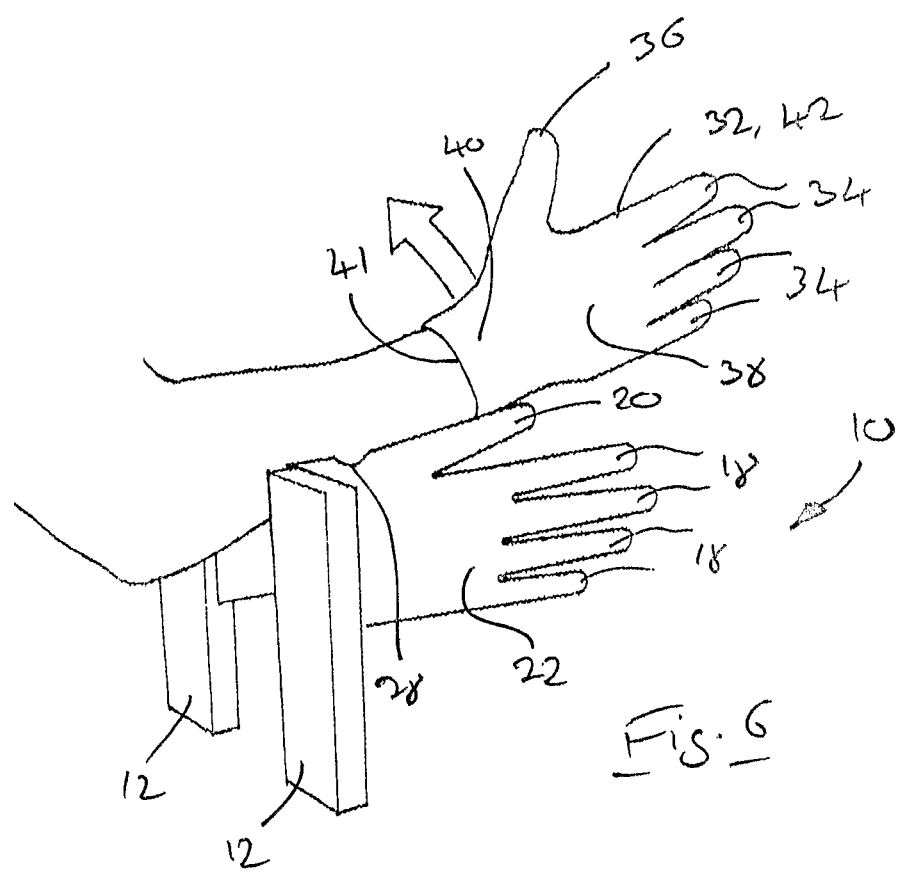
Figures 7A, 7B:
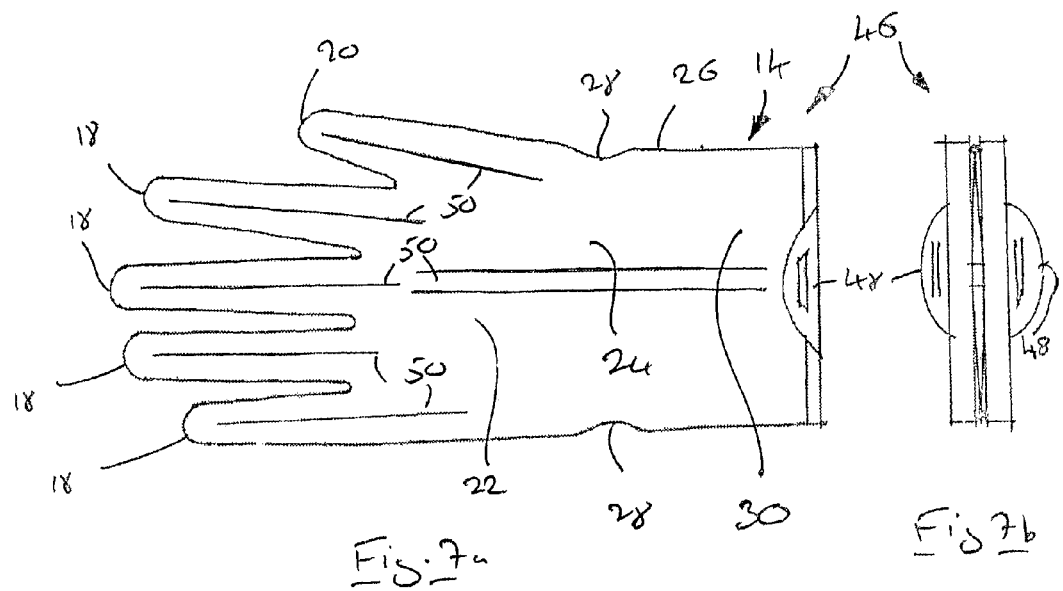
FIGS. 7a and 7b show side and end views of a second embodiment of a glove holding device according to an aspect of the present invention.

The thumb and fingers of the user are subsequently received in the finger and thumb portions 34,36 of the glove 32 as shown in FIG. 3. Continued movement of the hand 42 of the user in the direction of arrow 44 disengages the cuff bead of the glove 32 from the cut outs 28 and the holding members 14 begin to withdraw from the glove 32 through the cuff aperture 41. The flexible nature of the holding members 14 permits said holding members 14 to bend and resiliently deform sufficiently to enable their removal from the glove 32 without snagging on either the glove 32 or the hand 42 of the user. The low friction surface of the holding members further ensures that the holding members 14 can be removed from the glove 32 without snagging. The user is then able to move their gloved hand upwards and away from the opposing devices 10 (FIGS. 5 and 6). The substantially horizontal orientation of the holding members 14 and the direction of movement of the hand 42 of the user is not limiting and it will be appreciated that other orientations and directions are possible.

Movement of the hand of the user upwards and away from the holding members 14 is required in the context of the described embodiment. It will be appreciated that, depending upon the configuration of the devices 10, movement of the hand of the user may be required in other directions in order to remove the holding members 14 from the glove 32. The above described embodiment requires the holding devices 10 to remain stationary while the hand 42 of the user is moved. In alternative embodiments it will be understood that the hand of the user 42 may remain stationary while the devices 10 move relative thereto in order to effect donning of the glove 32. In yet a further embodiment, movement of both the hand 42 of the user and the devices 10 relative to one another may be required in order to effect donning of the glove 32.

It will be appreciated that the presence of the holding members 14 within the glove 32 ensures that the minimal contact is made between the hand 42 of the user and the material of the glove 32 until the tips of the fingers of the user are located within the respective finger portions 18,20 of the glove and the holding members 14 are withdrawn. This feature is advantageous in that it assists a user with a wet, damp or sweaty hand 42 to easily don a glove 32, particularly a latex glove or a glove of a similar material, as the hand 42 of the user moves easily between and over the holding members 14 without catching or snagging.

FIGS. 7a to 8b show an alternative embodiment of a glove holding device generally designated 46. Features common to the previously described embodiment are identified with like reference numerals. The device 46 comprises a pair of flexible holding or support members 14 having, as before, finger, thumb, palm, cuff and alignment portions 18,20,22,24,30. The alignment portions 30 are each provided with a tab 48 which, as will be described in greater detail below, enables the device 46 to be gripped by the free hand of the user. The finger, thumb, palm, cuff and alignment portions 18,20,22, 24,30 are provided with score lines 50 which promote the bending of the portions 18,20,22,24,30 to assist with the initial fitting of a glove to the device 26, the insertion of a user's hand between the members 14 and the subsequent withdrawal of the members 14 from the glove.

Figures 8A, 8B:
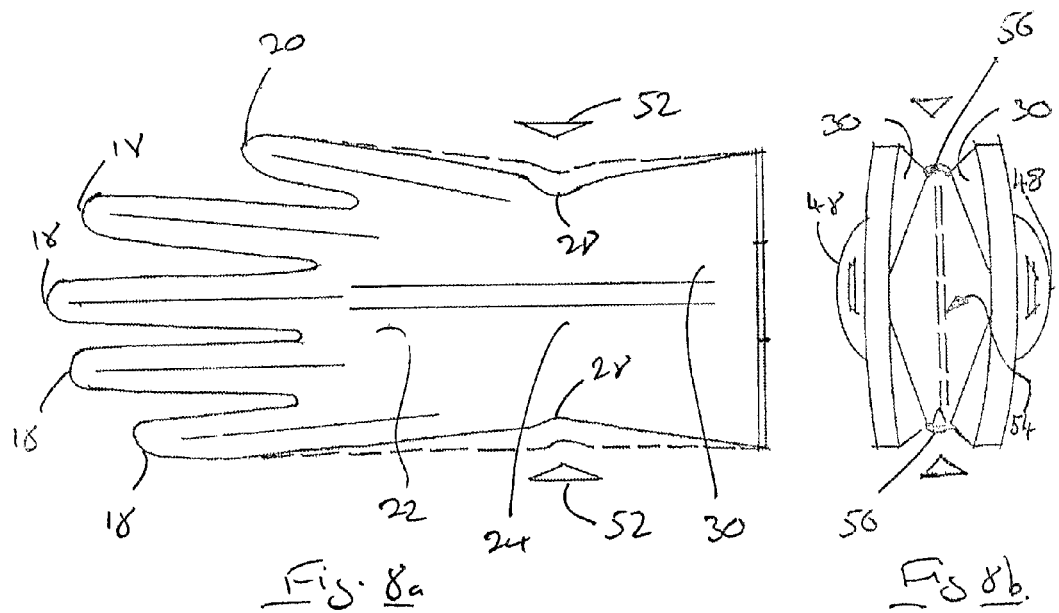
FIGS. 8a and 8b show further side and end views of the device of FIGS. 7a and 7b.

The members 14 are joined to one another in the region of the cut outs 28. As can be seen in FIG. 8b, this enables each member 14 to bow outwardly with respect to the opposite member when the members 14 are pinched as indicated by arrows 52. When pinched in this manner an aperture 54, as opposed to a slot, is provided between the cuff portions 24 into which a user may insert their hand. One or both of the joins 56 between members 14 is/are breakable so as not to impede the passage of a user's hand between the members 14 or the subsequent withdrawal of the members 14 from the glove 32.

FIGS. 9 to 11 illustrate the donning of a glove 32 using the device 46 of FIGS. 7a to 8b. The glove 32 is mounted to the device 46 as before, and the glove/device combination 32/46 is provided within a sealed cover 58. The cover 58 acts to maintain the sterility of the glove 32 prior to donning and, in the embodiment shown, is itself glove shaped. The cover 58 may be provided in other configurations such as, for example, that of a mitten or simply a bag. The cover 58 is provided with a tear open portion 60 in the region of the device cuff and alignment portions 24,30 which is removed immediately prior to donning.

With the tear open portion 60 removed, the members 14 are pinched by the free hand of the user as indicated by arrows 52. The user can then insert their other hand 42 into the aperture 45. Once the hand 42 has been thus inserted, the user can then grip one of the tabs 48 as shown in FIG. 10 before inserting their hand fully into the glove 32. The passage of the user's hand into the glove breaks one or both of the joins 56. As with the previously described embodiment, the members 14 are of sufficient flexibility to deflect around the hand 42 of the user and thus not impede the movement of the hand 42 into the glove 32. The respective thumb and finger portions of the members 14 guide the digits of the user into the corresponding thumb and finger portions of the glove 32. The members 14 can then be withdrawn from the glove 32 by the user as shown in FIG. 11. Where both joins 56 have been broken, it will be understood that each member 14 may need to be withdrawn separately.

It will be appreciated that as a result of the above procedure the glove 32 is donned to the hand 42 of the user with the glove shaped cover 58 remaining. This enables the user to don a glove to their remaining hand without compromising the sterility of the first glove 32. Once both gloves have been donned the covers 58 can be removed.

The embodiments described above refer to gloves 32 having five fingers. It will be understood that the device and method of the present invention may be used with gloves having alternative configurations, for example mittens. The embodiments described above further illustrate holding members where the finger, thumb, palm and cuff portions thereof are substantially the same size and shape as the corresponding portions of the glove. It will be appreciated that in alternative embodiments portions of the holding members may differ in size and shape to that of the glove. In particular, the longitudinal dimensions of portions of the holding members may be shorter than the corresponding portions of a glove. The glove may thus require to be gathered, concertinaed or otherwise folded when mounted to the holding members. In yet a further embodiment, the cuff portion of the glove may be folded inside out such that it at least partially overlaps the palm portion of the glove. In such an embodiment, the holding members may be configured such that they engage the cuff portion and reverse this folding as the glove is donned.

Looking now at FIG. 12 there is shown a flexible glove holding or support member generally designated 114. The holding member 114 is comprised of a substantially planar flexible sheet of material which, when folded in the manner described below, conforms to the shape of a glove. The member 114 is provided with finger portions 118 and a thumb portion 120. The finger and thumb portions 118,120 may correspond to the finger and thumb lengths of the glove to which the member 114 is to be fitted. Alternatively, the finger and thumb portions 118,120 may be shorter than the finger and thumb lengths of the glove to which the member 114 is to be fitted. In such an embodiment, the fingers and thumb of the glove may be folded, rolled or otherwise reduced in length to fit to the shorter finger and thumb portions 118,120 of the member 114. The finger portions 118 extend from a palm portion 122, which in turn extends from a cuff portion 124 of the member 114. It will be understood that the finger, thumb, palm and cuff portions 118,120,122,124 of the flexible member 114 define the glove support portion. An attachment portion 112 extends from the cuff portion 124 in the opposite direction to the palm portion 122. The cuff portion 124 is wider than the palm portion 122 as can be seen from FIG. 12. The width of the cuff portion 124 may be such that a glove fitted thereto is stretched slightly and thus retained to the cuff portion by frictional contact.

The thumb portion 120 extends laterally from a thumb base portion 123. The thumb base portion 123 extends from an edge 125 of the cuff portion 124 of the holding member 114 and is foldable over the palm and cuff portions 122,124. The thumb base portion 123 is foldable over the palm and cuff portions 122,124 along the fold line indicated by broken line 127.

Figure 13:
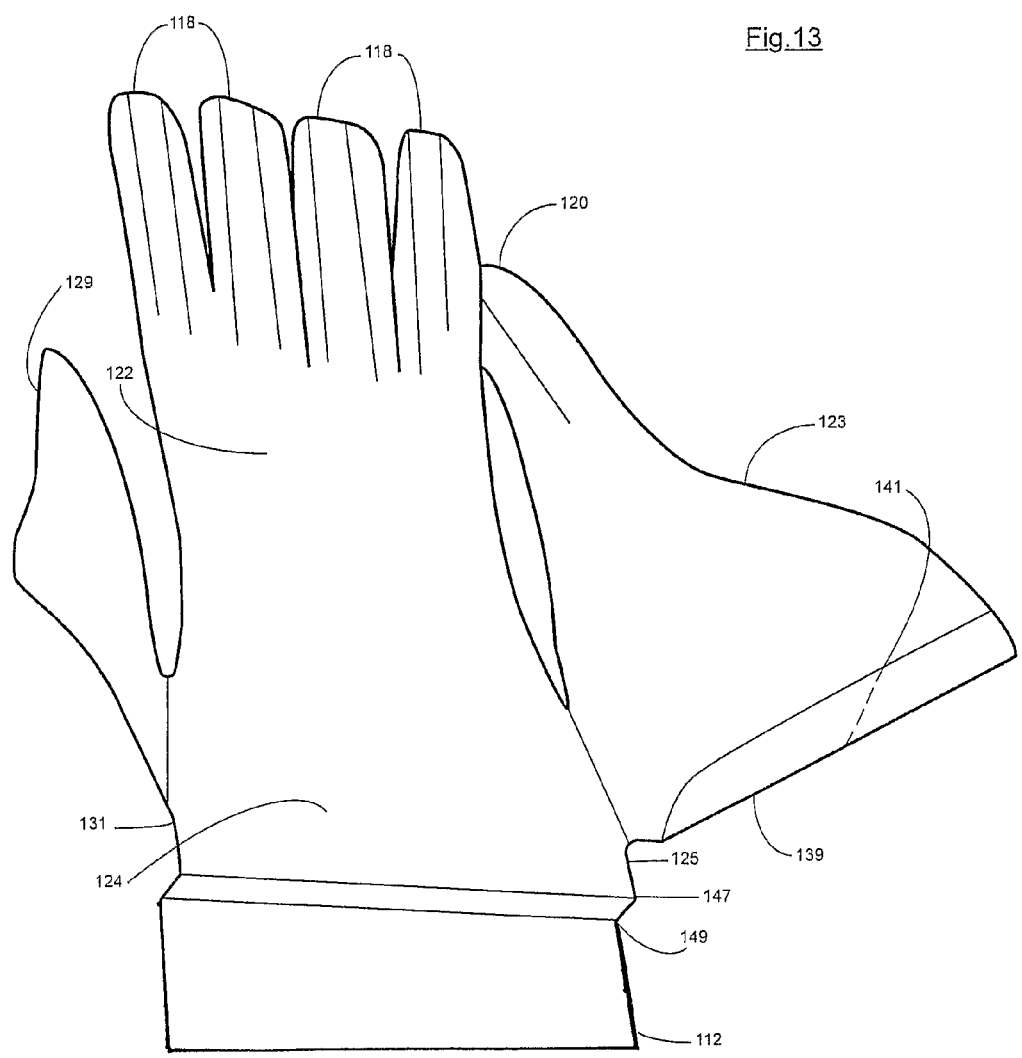
FIGS. 13 and 14 show perspective views of the glove holding member of FIG. 12.
Figure 14:
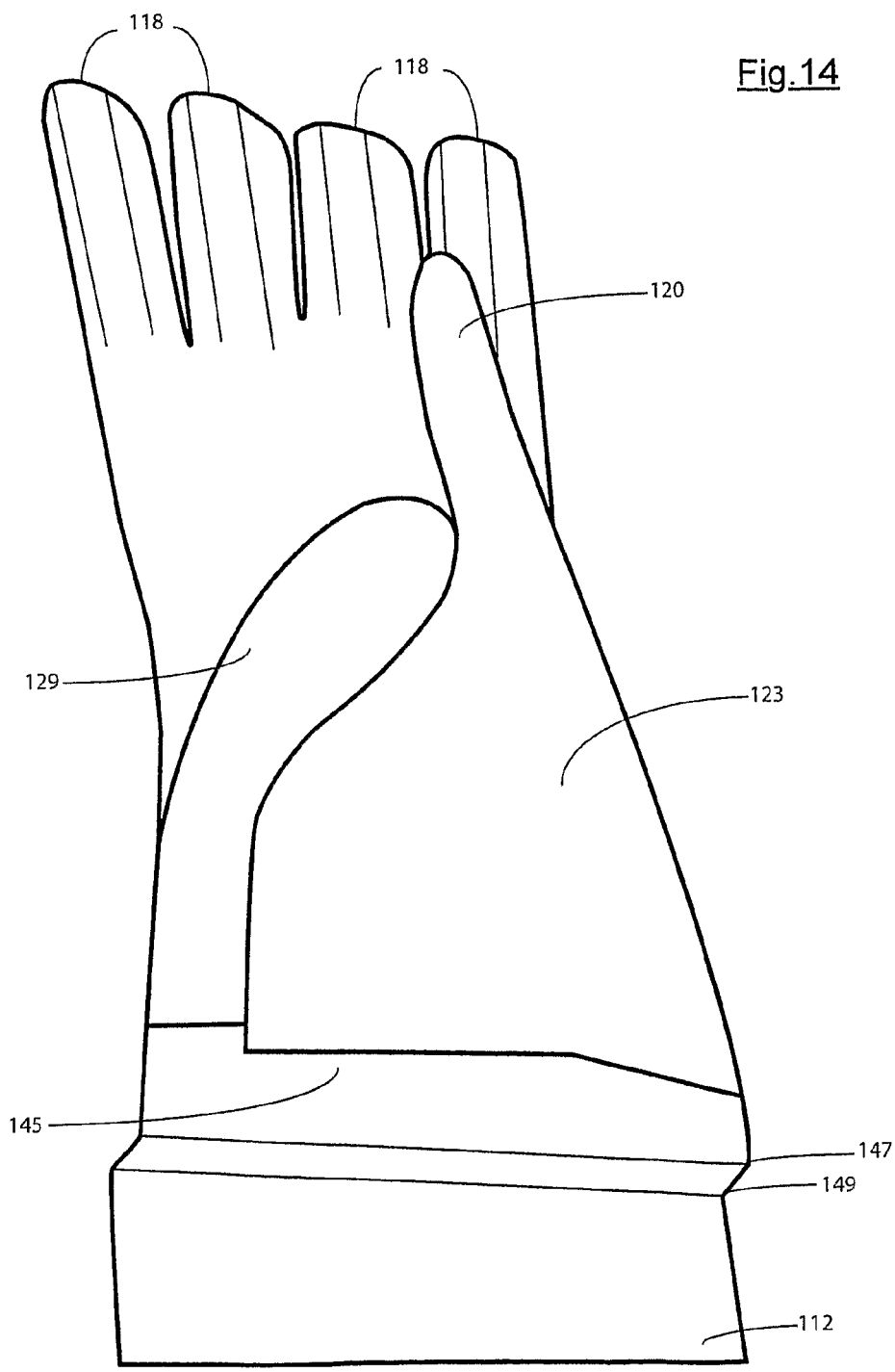

The holding member 114 is further provided with a flap 129 which extends from an opposite edge 131 of the cuff portion 124 to the edge 125 from which the thumb base portion 123 extends. The flap 129 is foldable over the palm and cuff portions 122,124 along the fold line indicated by broken line 133. Both the thumb base portion 123 and the flap 129 have an edge 135,137 which is proximal to the cuff portion 124 of the member 114 and distal to the finger portions 118. The thumb base portion edge 135 is foldable over the thumb base portion 135 along the fold line indicated by broken line 139 to form a "V" shaped channel 141. This channel 141 can be seen in FIG. 13. The flap edge 137 is similarly foldable over the flap 129 along the fold line indicated by broken line 143 to form a "V" shaped channel. The respective "V" shaped channels can be engaged with one another when the thumb base portion 123 and flap 129 are folded over the palm and cuff portions 122,124 to releasably retain the thumb base portion 123 and flap 129 with one another. This arrangement can be seen in FIG. 14 where the flap 129 is provided innermost between the thumb base portion 123 and the palm portion 122 of the member 114. With the thumb base portion 123 and the flap 129 retained together in this manner, there is defined a mouth 145 between the thumb base portion 123, flap 129 and cuff portion 124 of the holding member 114.

Between the cuff portion 124 and the attachment portion 112 there are provided a pair of space fold lines 147,149 which allow the cuff portion 124 to be folded back upon the attachment portion 112 to effectively shorten the overall length of the holding member 114. This serves the purpose of assisting with the packaging of the holding member 114 in a packaging arrangement as will be described in greater detail below. The fold lines 147,149 further serve the purpose of slightly elevating and tilting the mouth 145 in the direction of a user when donning a glove.

The holding member 114 is formed from a flexible material such as, for example, PVC. The finger and thumb portions 118,120 are provided with score or crease lines 151 which serve to contour the thumb and finger portions.

Figure 15:
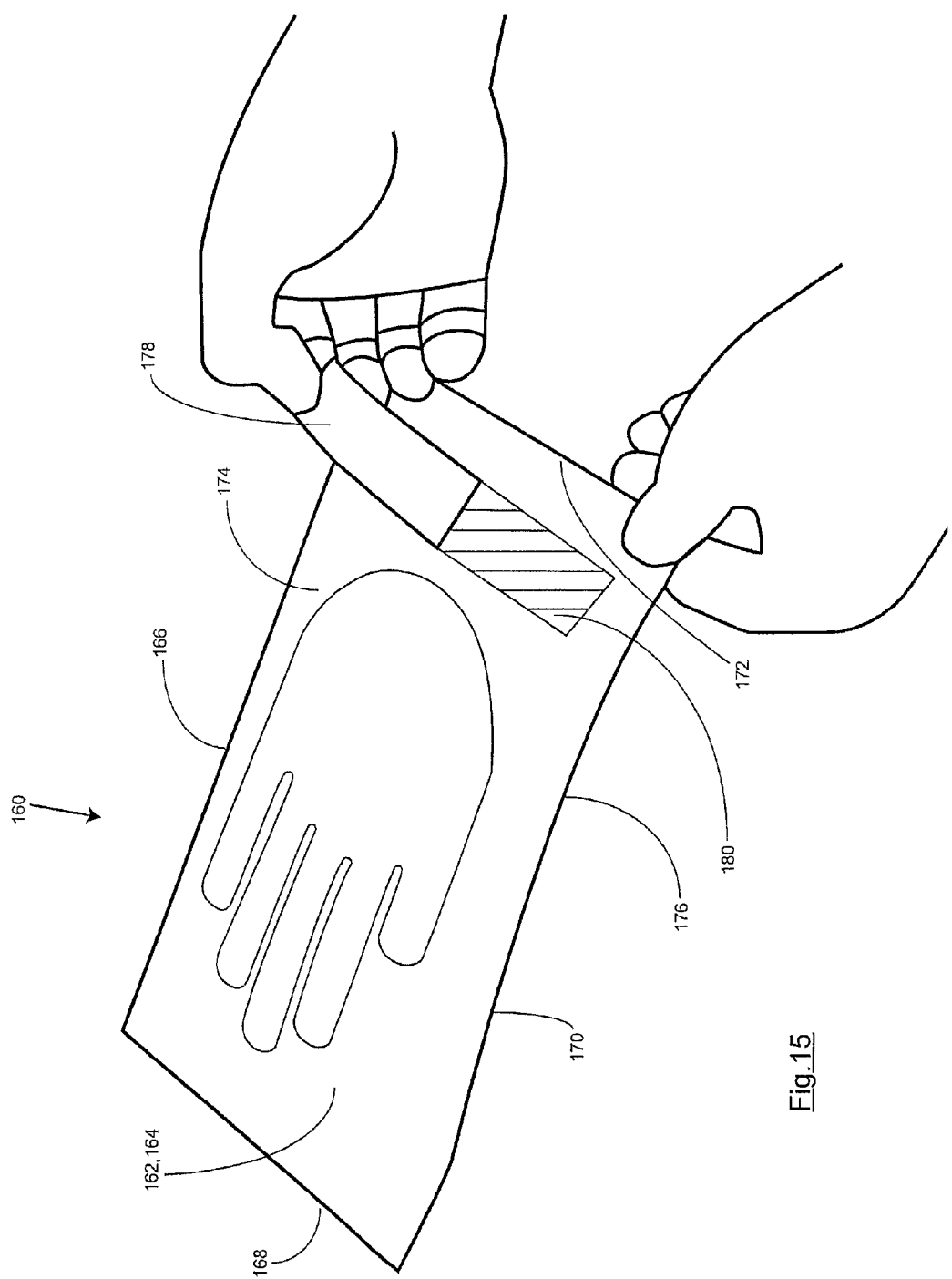
FIGS. 15 to 20 show perspective views of a packaging arrangement containing glove holding members of the type shown in FIGS. 12 to 14.

Referring now to FIGS. 15 to 20 there is shown a packaging arrangement, generally designated 160, within which the holding member 114 described above is incorporated. The arrangement 160 comprises a packet 162 formed from a single sheet of material 164. In the embodiment shown, the sheet of material 164 is folded along one edge 166 in a manner similar to the cover of a magazine, and is sealed along the non-folded edges 168,170,172. Each face 174,176 of the packet 162 is provided with a removable strip 178 which covers a layer of adhesive 180. FIG. 15 shows one of the strips 178 being removed to reveal the adhesive 180. In an alternative embodiment, the packet may be provided with a single layer of adhesive 180 which extends across both faces 174, 176 of the packet 162. The packet 162 may be provided alternative means to locate it to a surface and to resist movement thereof during donning of a glove. For example, the exterior of the packet 162 may be provided with a strip of hook and loop fastener material which, in use, engages with a corresponding portion of hook and loop fastener material at a donning location. The exterior of the packet 162 may be provided with a portion of a fastener which connects to a corresponding fastener portion at a donning location. In yet a further embodiment, there may be provided a high friction, non-slip coating on the exterior of the packet 162 which, in use, resists movement of the packet 162 over a surface upon which it rests during donning of a glove.

Figure 16:
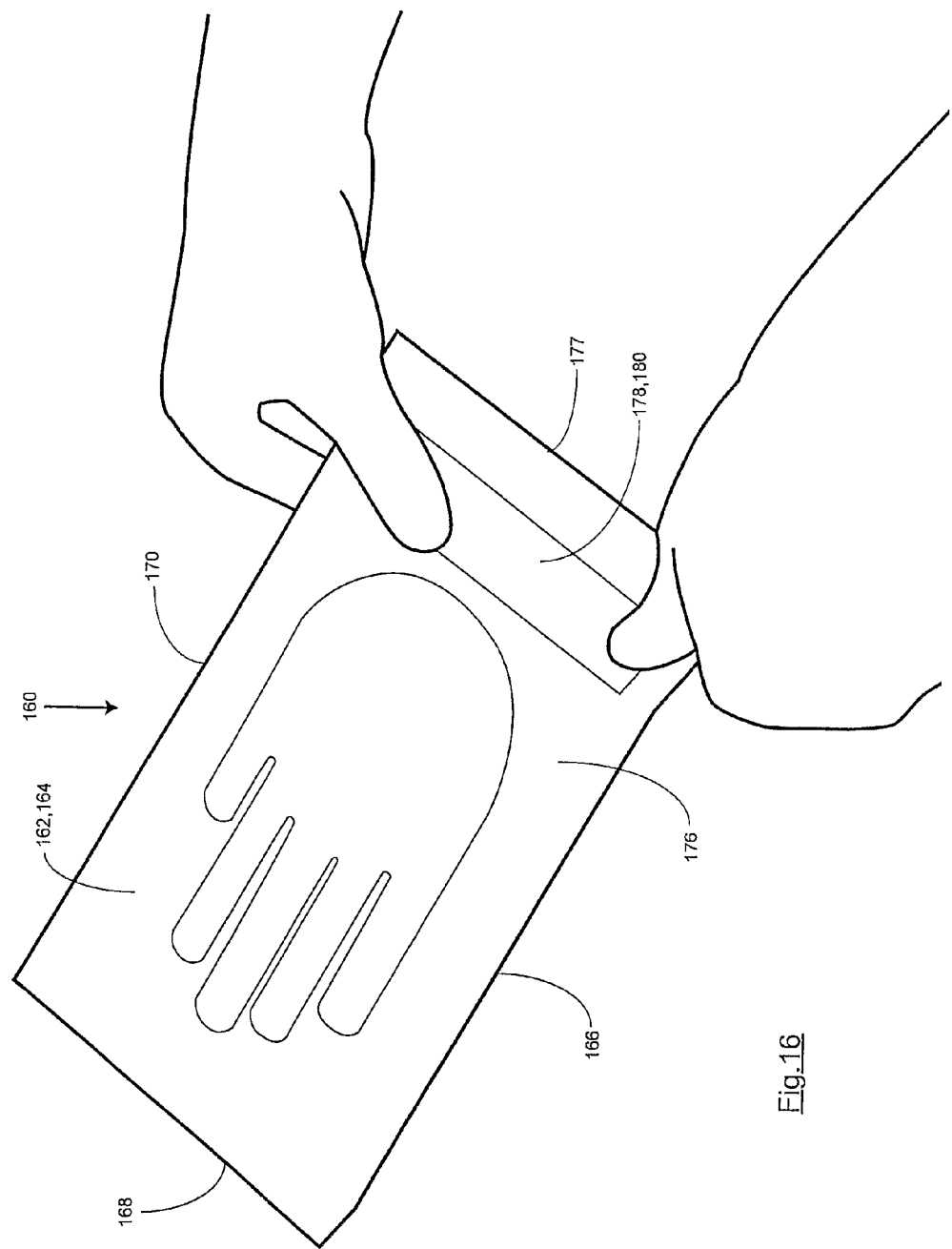
Figure 17:
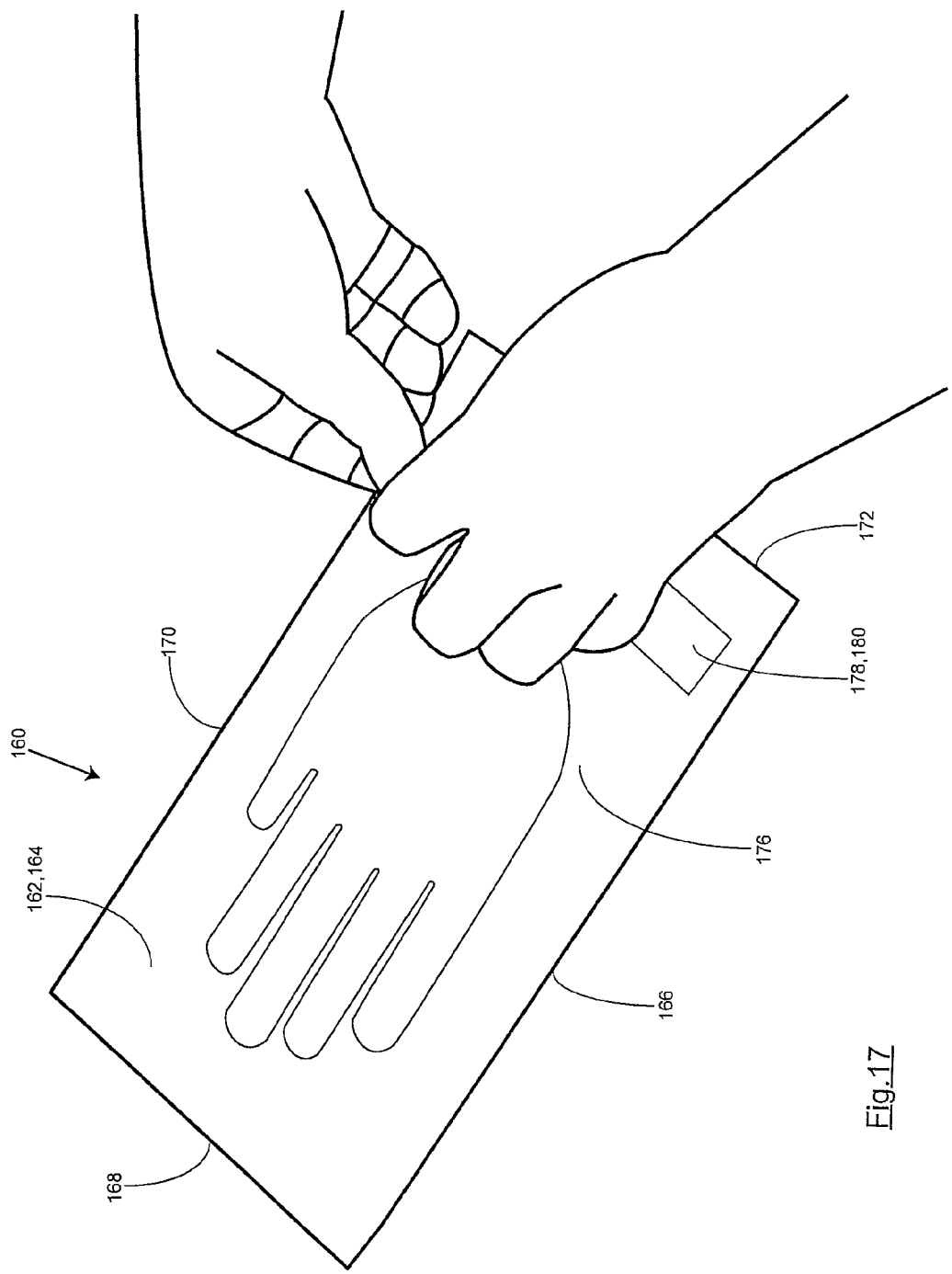

Prior to the opening of the packet 162, one of the strips 178 is removed and the packet attached to an appropriate surface by the adhesive (FIG. 16). The surface may for example be a table, wall, floor or any other suitable place to which the packet can be attached to facilitate donning of the gloves contained within the packet 162.

Figure 18:
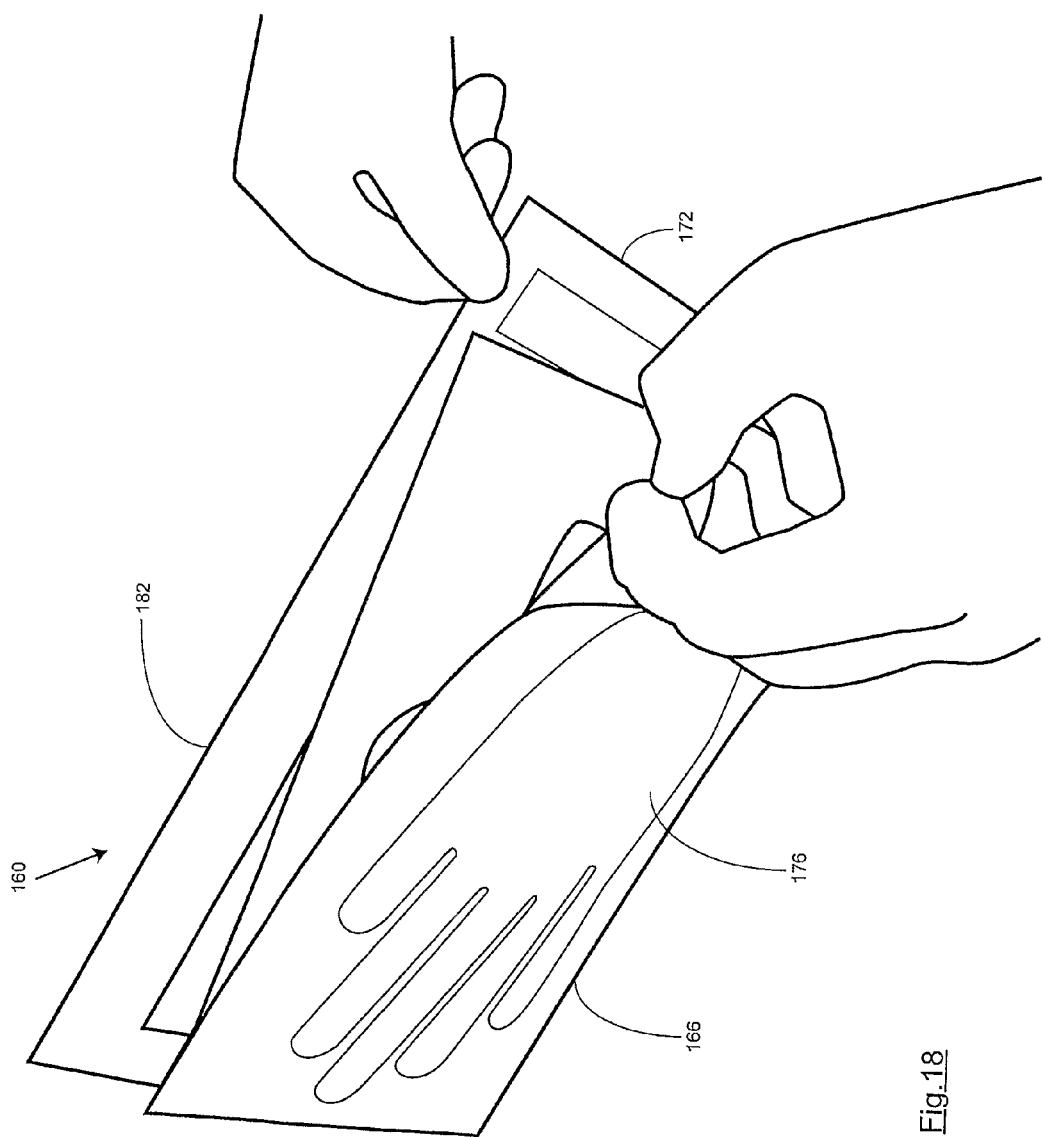

Once the packet 162 has been attached to a surface, the seals provided along the non-folded edges 168,170,172 can be opened (FIG. 17) and the packet 162 opened in the manner of a book or magazine (FIG. 18). Prior to the opening of the packet 162 a user may remove the strip 178 presented uppermost to reveal the second strip of adhesive 180. This enables the packet 162 to be attached to the surface by the second strip of adhesive 180 when fully opened.

Figure 19:
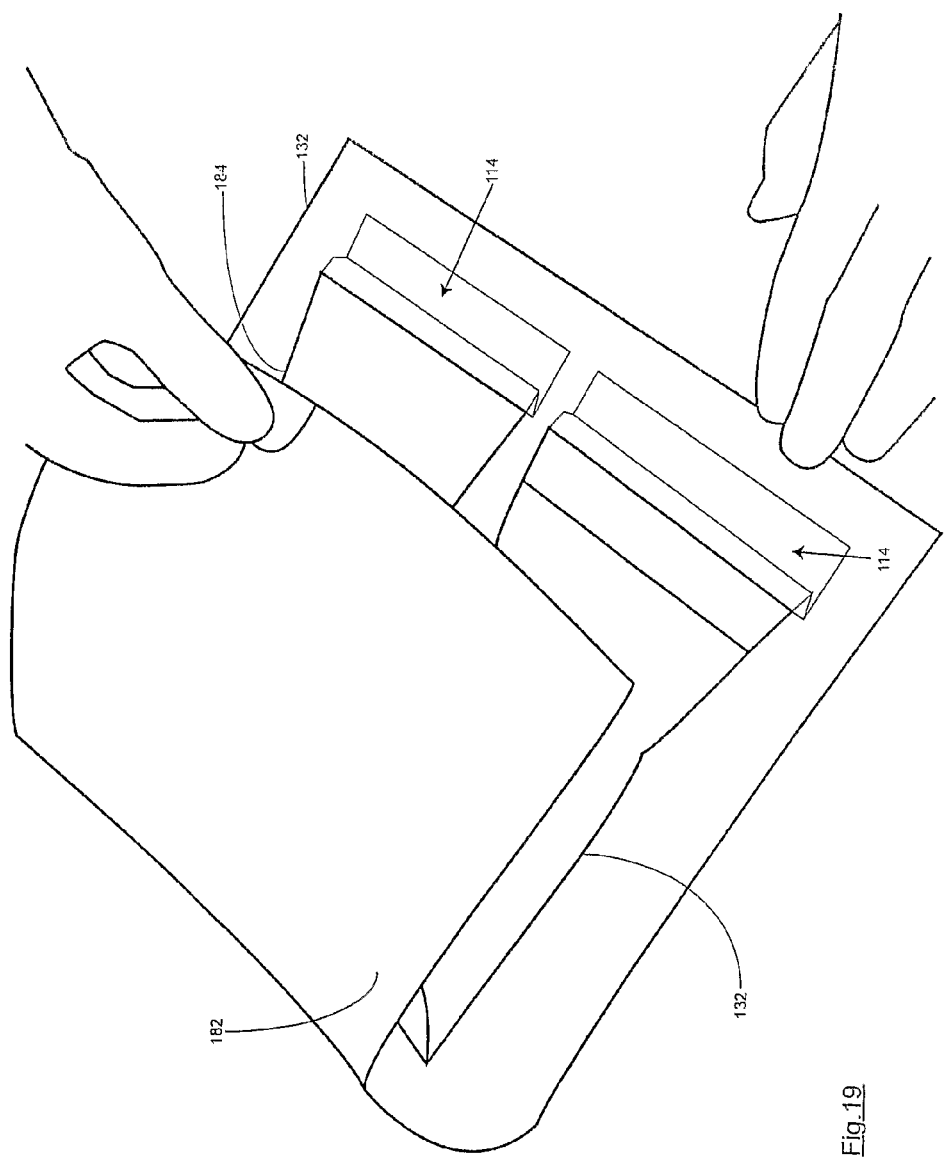

FIG. 19 shows the packet 162 fully opened and a cover sheet 182 being lifted from two glove holding members 114 and associated gloves 132 contained within the packet 162.

Figure 20:
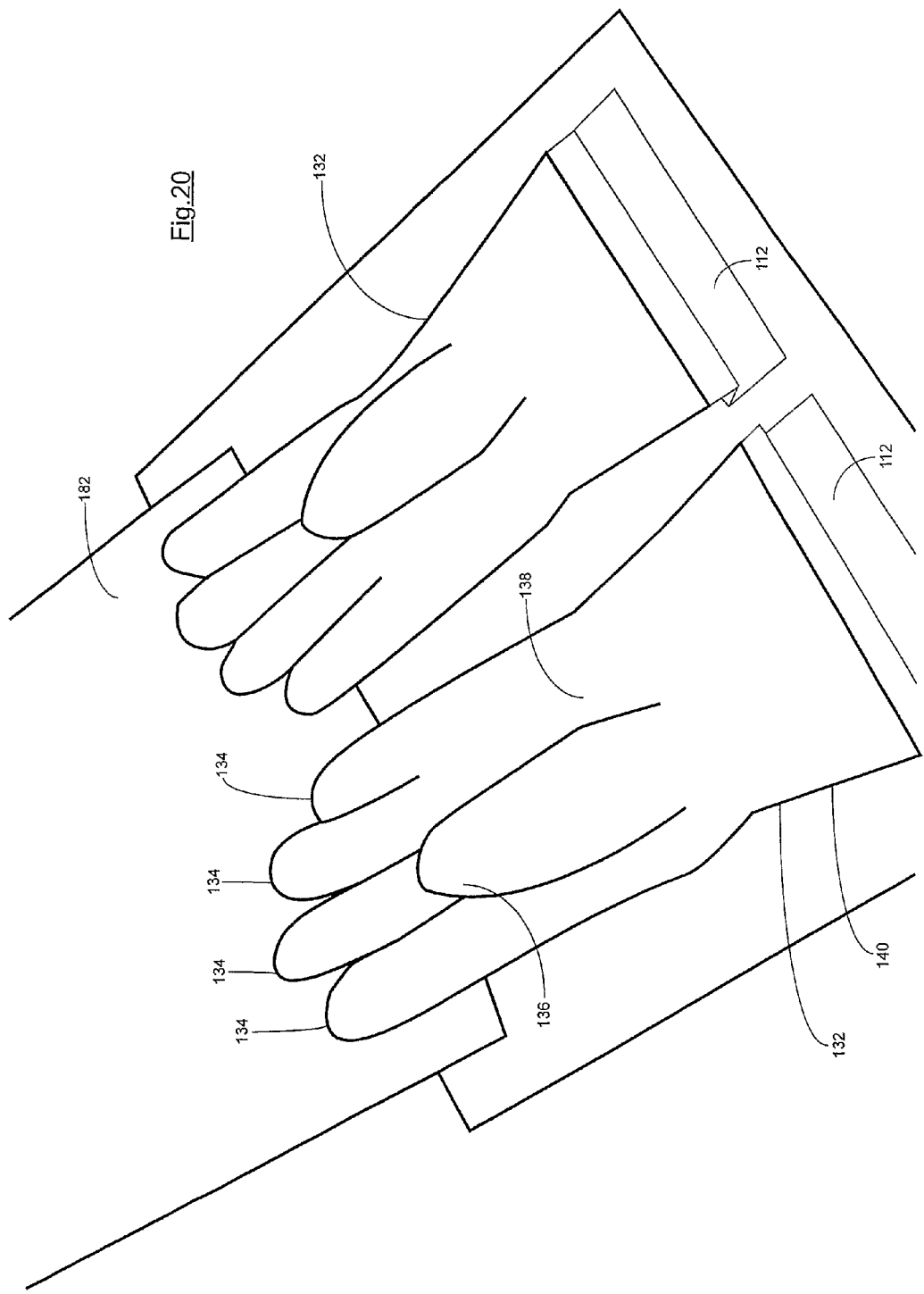

The cover sheet 182 is provided with a tab 184 which enables the cover sheet 182 to be lifted by a user without having to touch the remainder of the cover sheet 182. In an alternative embodiment, the tab 184 may be replaced by a flap which extends along an edge of the cover sheet 182. The tab 184 or flap may be marked or colour coded to indicate to a user that it is to be gripped in order to deploy the cover sheet 182. Prior to the opening of the packet 162 the cover sheet 182 separates the gloves 132 from one another and prevents rubbing or fretting of the gloves 132. The cover sheet is fixed along an edge thereof to the interior of the packet and can be moved to a deployed position outside of the packet 162 as shown in FIG. 20. The cover sheet 182 thus acts to prevent one or both of the gloves 132 coming into contact with the surface to which the packet 162 is adhered during donning of the gloves 132 by a user.

As can be seen from FIG. 20 each glove 132 is mounted to a respective holding member 114 such that it is presented palm and thumb uppermost. Each holding member 114 is attached by the attachment portion 112 thereof to the inner surface of the sheet of material 164 forming the packet 162. In such an embodiment it will be understood that each holding member 114 may have been cut from a sheet of material before being attached to the packet 162. In an alternative embodiment, each holding member 114 may remain connected to such a sheet of material via the attachment portion 112, with said sheet of material being attached to the packet 162. In yet a further embodiment each holding member 114 may remain connected to such a sheet of material via the attachment portion 112, and said sheet of material, together with a glove, subsequently being sealed in a bag like package. In such an embodiment the sheet is not attached to the interior of the bag like package and may be removed fully therefrom for donning of the glove. Each glove 132 is mounted to a holding member 114 such that the finger, thumb, palm and cuff portions 118,120,122,124 of the holding member 114 aligns with the corresponding finger, thumb, palm and cuff portions 134,136,138,140 of the glove 132. The width of the holding member cuff portion 124 is such that the cuff 140 of the glove 132 is stretched slightly and thus retained to the holding member 114 due to the resilient nature of the glove material.

Figure 21:
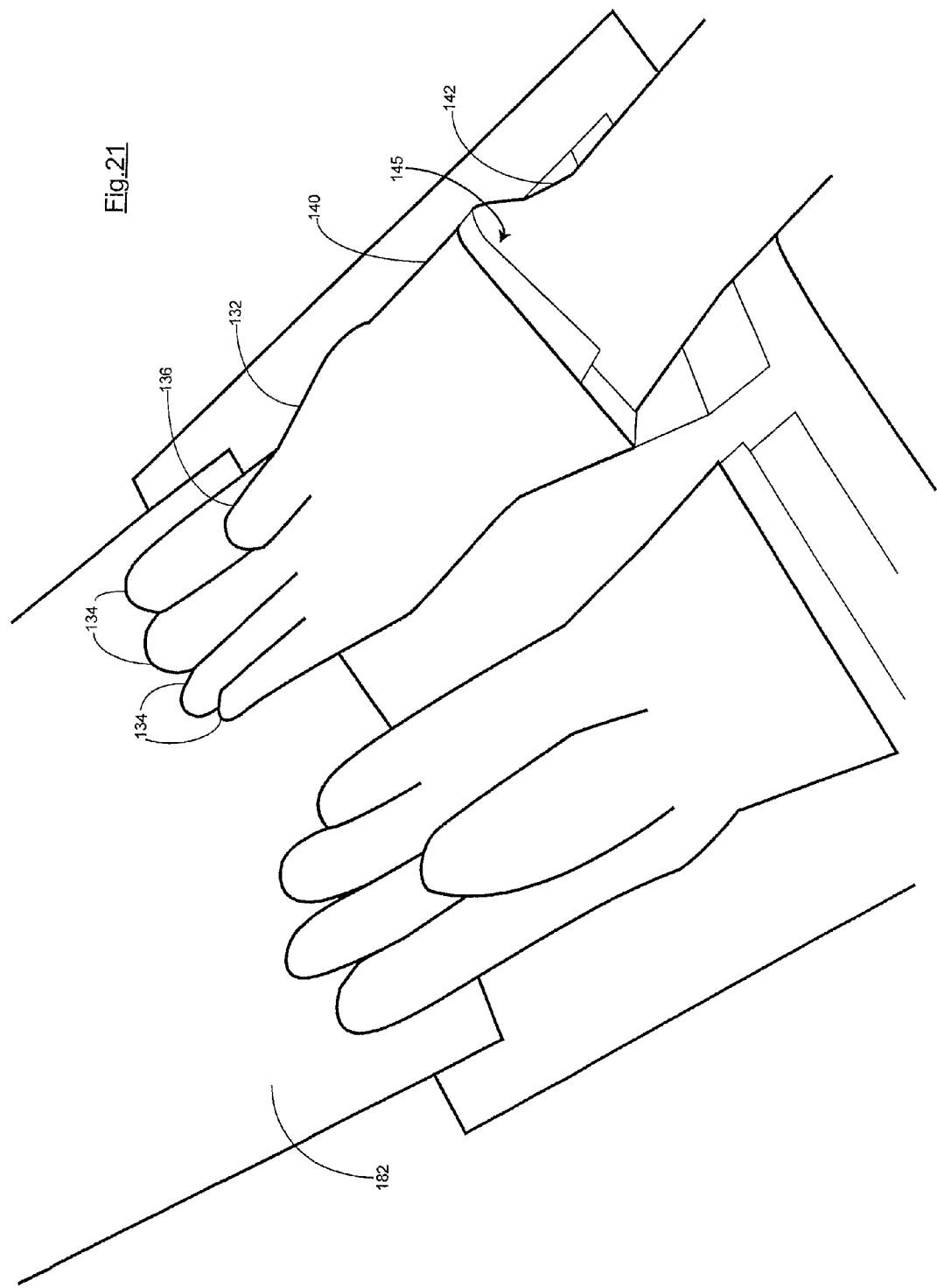
FIGS. 21 to 23 show the donning of a glove.

In use, a user inserts their hand 142 into the mouth 145 defined by the holding member 114 (FIG. 21). Continued movement of the hand 142 of the user expands the mouth 145 and allows the hand 142 of the user to enter the glove 132. The inter-engagement of the "V" shaped channels of the thumb base portion and flap 123,131 permits the mouth 145 to open without the thumb base portion and flap 123,131 becoming disengaged from one another. The material from which the holding members 114 are formed has a low friction surface and hence does not impede the passage of the hand 142 of the user.

Figure 22:
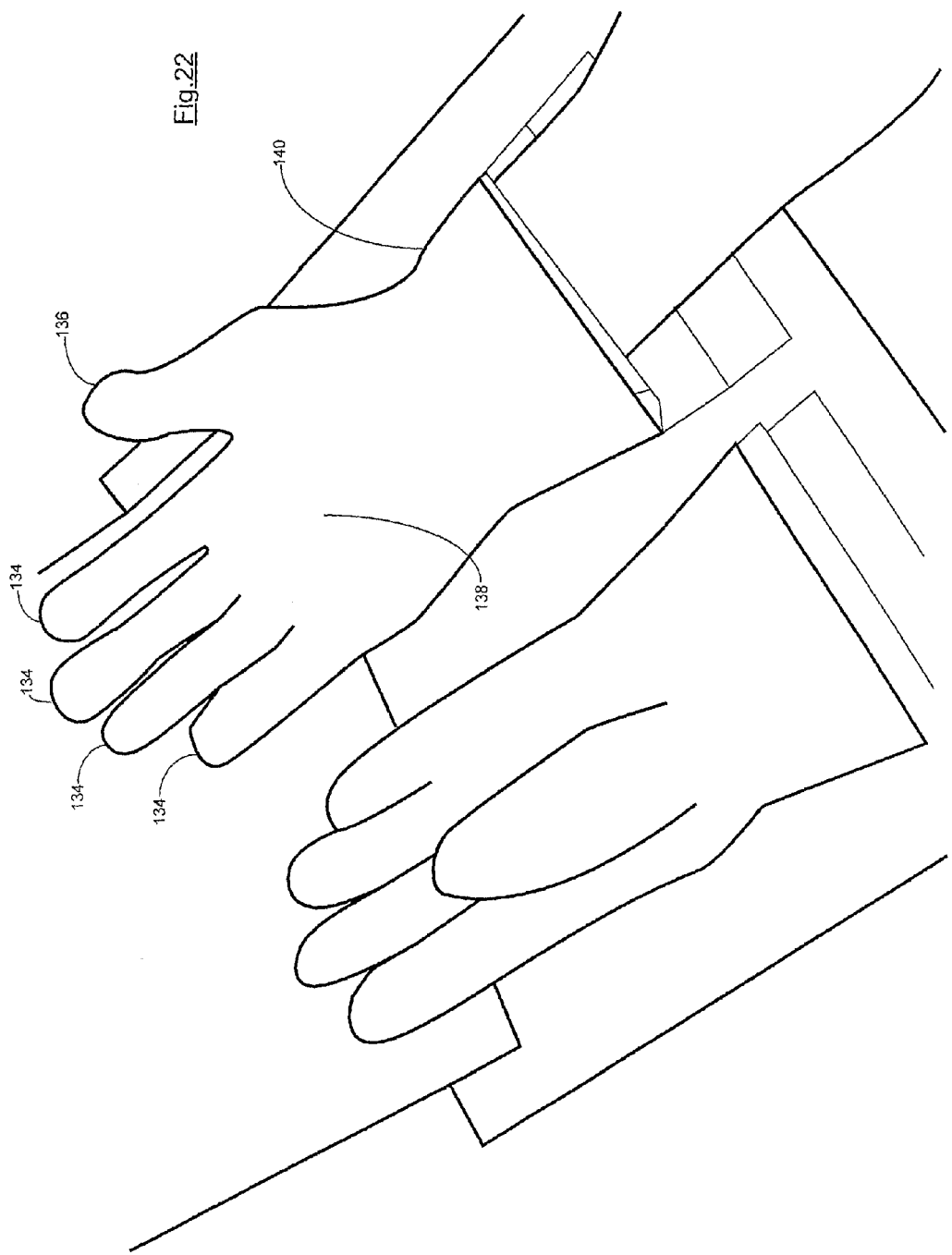
Figure 23:
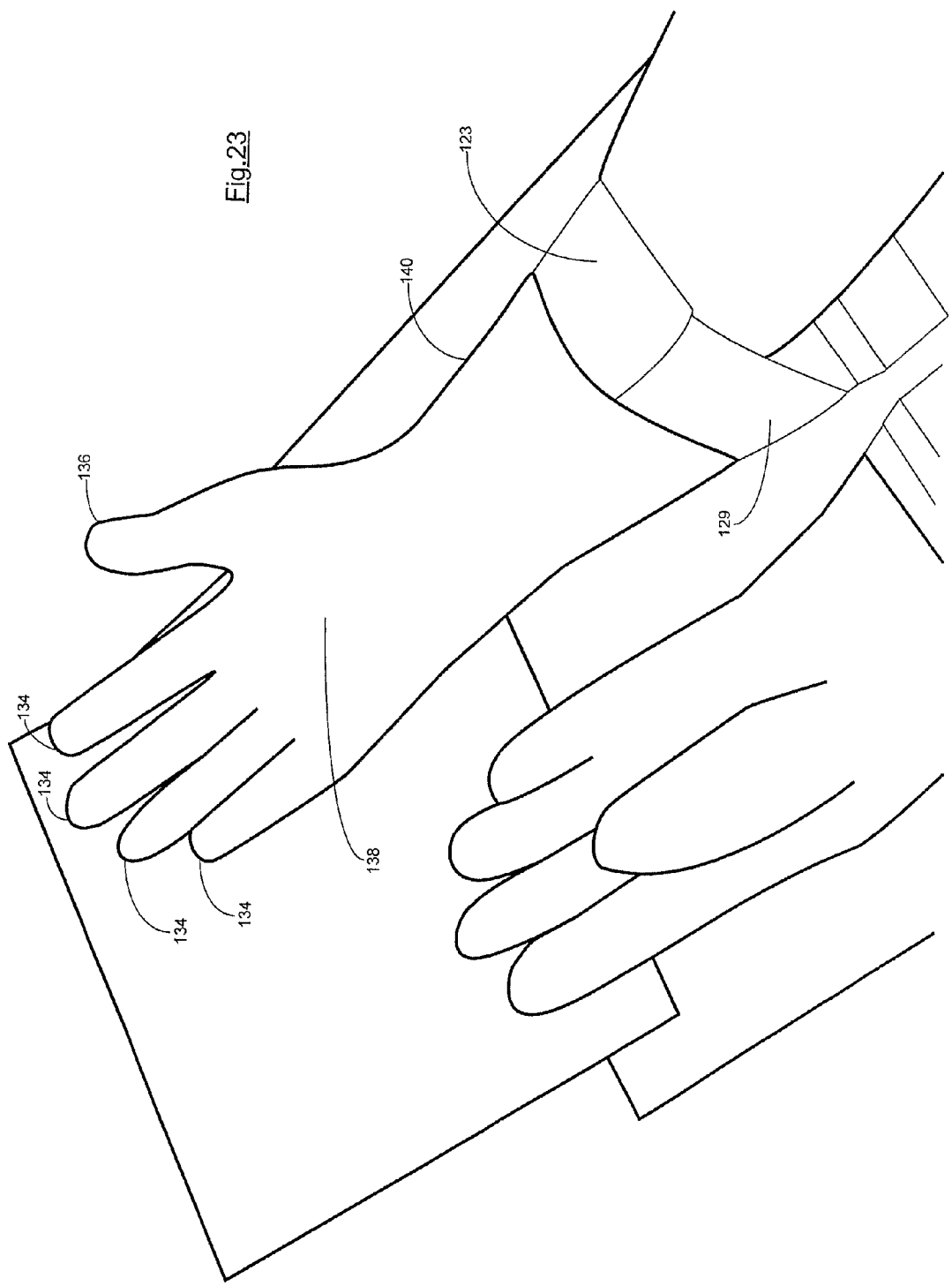

The thumb and fingers of the user are subsequently received in the finger and thumb portions 134, 136 of the glove 132 as shown in FIG. 22. The thumb and finger portions 118,120 of the holding member guide the thumb and fingers of the user into the corresponding portions 134.136 of the glove 132. Continued movement of the hand 42 of the user disengages the cuff of the glove 132 from the cuff portion 124 of the holding member 114, and the holding member 114 begins to withdraw from the glove 132 through the cuff aperture thereof. The flexible nature of the holding member 114 permits the holding member 114 to bend and resiliently deflect sufficiently to enable their removal from the glove 132 without snagging on either the glove 132 or the hand 42 of the user. The low friction surface of the holding member 114 further ensures that the holding member 114 can be removed from the glove 132 without snagging. The user is then able to move their gloved hand upwards and away from the holding member 114. The connection of the packet 162 to a surface by one or more of the adhesive strips 180 provides the necessary resistance to movement of the holding members 114 which enables a user to don the gloves 132.

While the embodiment shown provides two gloves 132 and glove holding members 114 within the packet 162, it will be appreciated that only a single glove 132 and glove holding member 114 may be provided. The cover sheet 182 is optional and is preferably provided where sterility of the gloves 132 must be maintained during donning. It will further be appreciated that the glove holding member 114 need not be used in conjunction with a packet 162 of the type described and may be used in conjunction other packaging arrangements.

Figure 24:
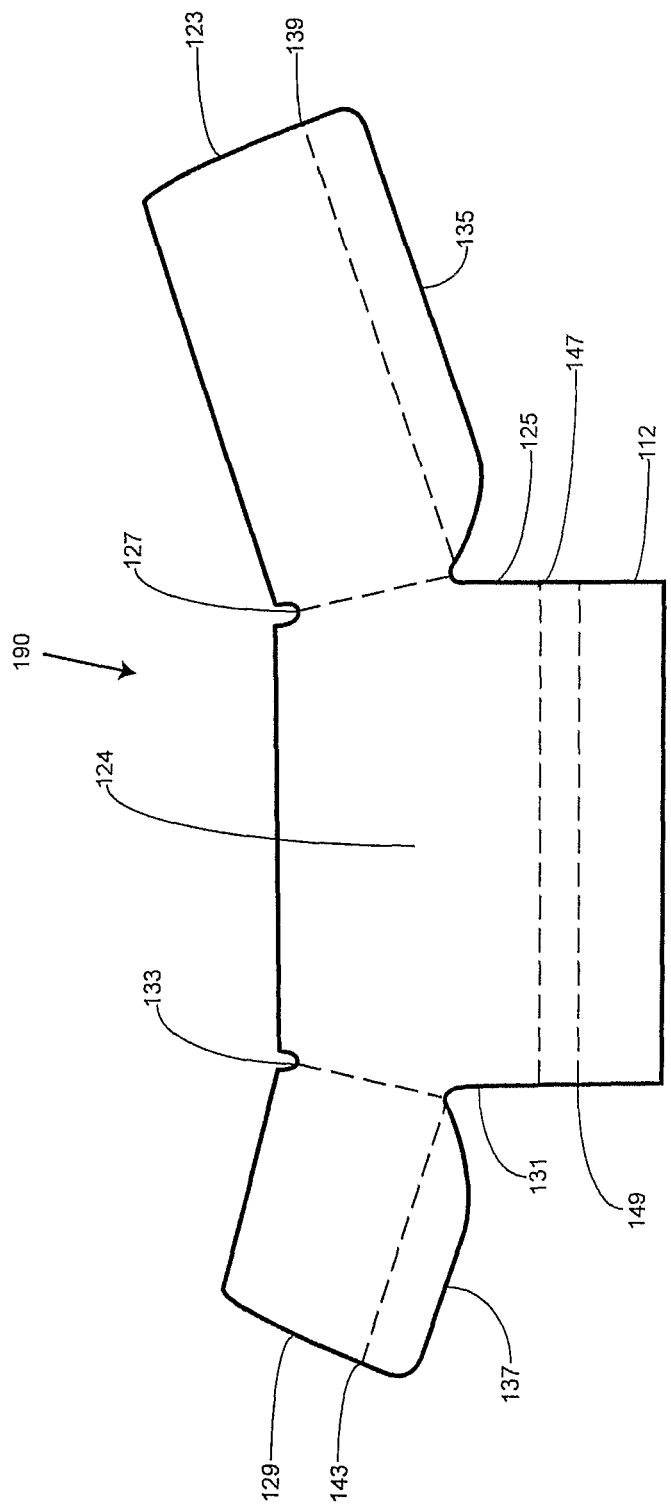
FIG. 24 shows a plan view of a further embodiment of a glove holding member according to an aspect of the present invention.

Referring now to FIG. 24, there is shown an alternative embodiment of a holding member generally designated 190. Features common to the holding member 114 described with reference to FIG. 12 are identified with like reference numerals. The holding member 190 differs from that described with reference to FIG. 12 in that the finger, thumb and palm portions 118,120,122 are omitted. The holding member 190 retains the cuff and attachment portions 124,112, together with laterally extending flaps 123,129. The flaps 123,129 are foldable over the cuff portion 124 as indicated by fold lines 127 and 133. The edges 135,137 of the flaps 123,129 proximal to the cuff portion 114 are foldable as described above to define "V" shaped channels which permit the flaps 123,129 to be slidably retained in association with one another.

In use, the holding member 190 can be fitted into the cuff region of a glove in the manner described above, with the glove being retained to the holding member 190 by the resilience of the glove material. A user wishing to don the glove inserts their hand into the mouth defined between the cuff portion 114 and the flaps 123,129 in the same manner as described above. The holding member 190 may be utilised in conjunction with a packet 162 of the type described above.

The holding members of the present invention may by packaged individually with a glove, or packaged in pairs. In a further embodiment, a plurality of holding members may be arranged together on a strip, reel or similar support arrangement. For example, there may be provided a plurality of right and left hand glove pairs supported upon corresponding holding members. The support arrangement may be incorporated into a dispensing mechanism which, in use, presents a pairs of gloves in sequence to a donning location. Alternatively, the dispensing mechanism may be provided with separate support arrangements for respective pluralities of left and right handed gloves.

The invention claimed is:

1. A flexible member for supporting a glove to be donned by a user, the flexible member having a glove support portion configured to extend into and across at least part of the interior of a glove and is fittable, in use, to the interior of a glove through the cuff aperture thereof, and an attachment portion by which the flexible member can be held to facilitate donning of a glove and the subsequent removal of the glove support portion from the cuff aperture of a glove while the glove is worn by a user, wherein the glove support portion is substantially planar and is of sufficient flexibility to deflect, deform, fold or bend, in use, in a predetermined manner around the hand and/or wrist of a user as said hand is inserted into a glove supported by the glove support portion, and further as the glove support portion is removed from the glove through the cuff aperture thereof.

2. A flexible member as claimed in claim 1 wherein the glove support portion of the flexible member is provided with formations which cause the member to deflect in said predetermined manner.

3. A flexible member as claimed in claim 1 wherein the glove support portion is provided with at least one digit portion which, in use, is received in a corresponding digit portion of a glove.

4. A flexible member as claimed in claim 1 wherein the attachment portion is provided with a formation connectable to a fixed base.

5. A flexible member as claimed in claim 1 wherein the attachment portion is configured so as to be grippable by a hand of a user.

6. A flexible member as claimed in claim 1 wherein the glove support portion is provided with a means to retain a cuff bead of a glove fitted to the flexible member.

7. A flexible member as claimed in claim 1 wherein the glove support portion is provided with means to hold the cuff of a glove supported thereby in an open position.

8. A flexible member as claimed in claim 7 wherein the flexible member is provided with an extension of the glove support portion, which extension, in use, is positioned in the region of the cuff of glove supported by the glove support portion.

9. A flexible member as claimed in claim 8 wherein the extension extends laterally from an edge of the cuff portion.

10. A device for holding a glove in a manner whereby it can be readily donned by a user without touching the exterior of the glove, the device comprising two flexible mounting members according to claim 1.

11. A device as claimed in claim 10 wherein the flexible members are joined to one another at at least one location, 12. A device as claimed in claim 11 wherein the flexible members are joined to one another at two locations.

13. An apparatus for the donning a glove by a user without touching the exterior of the glove, the apparatus comprising the combination of a flexible member as claimed in claim 1 and a glove supported on the flexible member.

14. An apparatus for the donning a glove by a user without touching the exterior of the glove, the apparatus comprising the combination of a device as claimed in claim 10 and a glove supported on the device.

15. An apparatus as claimed in claim 13 wherein the apparatus sealed within a cover which is at least partially removable before use of the apparatus.

16. An apparatus as claimed in claim 13 wherein the apparatus is provided within a container, the container being openable to allow access to the glove, wherein the container is provided with attachment means to releasably attach the container to a surface.

17. An apparatus according to claim 13, wherein the glove comprises a sterile glove.

18. An apparatus according to claim 13, wherein the glove comprises a surgical or laboratory glove.

19. An apparatus according to claim 13, wherein the glove comprises a glove for use in a manufacturing environment and/or in the preparation of food.

20. An apparatus according to claim 13, wherein the glove comprises a non-sterile glove.

* * * * *